(12) United States Patent  
Christoph et al.

(10) Patent No.: US 9,025,855 B1  
(45) Date of Patent: May 5, 2015

(54) METHOD FOR MEASURING AN OBJECT

(75) Inventors: Ralf Christoph, Giessen (DE); Ingomar Schmidt, Buseck (DE); Michael Hammer, Reiskirchen (DE); Thomas Wiedenhöfer, Pohlheim-Holzheim (DE)

(73) Assignee: Werth Messtechnik GmbH, Giessen (DE)

( * ) Notice: Subject to any disclaimer, the term of this patent is extended or adjusted under 35 U.S.C. 154(b) by 569 days.

(21) Appl. No.: 13/202,476

(22) PCT Filed: Feb. 19, 2010

(86) PCT No.: PCT/EP2010/052145
§ 371 (c)(1),
(2), (4) Date: Aug. 19, 2011

(87) PCT Pub. No.: WO2010/094774
PCT Pub. Date: Aug. 26, 2010

(30) Foreign Application Priority Data

| Feb. 20, 2009 | (DE) | .......................... | 10 2009 003 514 |
| Mar. 10, 2009 | (DE) | .......................... | 10 2009 003 597 |
| Apr. 24, 2009 | (DE) | .......................... | 10 2009 003 826 |
| May 20, 2009 | (DE) | .......................... | 10 2009 025 846 |
| Jul. 17, 2009 | (DE) | .......................... | 10 2009 026 198 |
| Aug. 24, 2009 | (DE) | .......................... | 10 2009 043 838 |
| Nov. 9, 2009 | (DE) | .......................... | 10 2009 044 476 |
| Nov. 18, 2009 | (DE) | .......................... | 10 2009 044 580 |

(51) Int. Cl.
*G01N 23/04* (2006.01)
*G06T 11/00* (2006.01)
*G06T 5/00* (2006.01)

(52) U.S. Cl.
CPC ............ *G01N 23/046* (2013.01); *G06T 11/005* (2013.01); *G06T 5/001* (2013.01)

(58) Field of Classification Search
CPC .................. G06T 7/0012; G06T 2207/10072; G06T 2207/10081; G06T 2207/10116; G06T 2207/30108; G06T 2207/30164; G01N 23/00; G01N 23/046; G01N 23/083; G01N 2223/3306; G01N 2223/419
USPC ............ 382/128, 131, 152; 378/4, 10, 11, 16, 378/20, 58
See application file for complete search history.

(56) References Cited

U.S. PATENT DOCUMENTS

| 5,119,408 A | 6/1992 | Little et al. .................... 378/4 |
| 5,319,693 A | 6/1994 | Eberhard et al. ................ 378/19 |

(Continued)

FOREIGN PATENT DOCUMENTS

| CN | 1268338 A | 10/2000 | ............... A61B 6/03 |
| CN | 1418353 A | 5/2003 | ............... G06T 5/00 |

(Continued)

OTHER PUBLICATIONS

European Office Action dated Jun. 18, 2012, corresponding to European Patent Application No. 10708956.7.

(Continued)

*Primary Examiner* — Andrew W Johns
(74) *Attorney, Agent, or Firm* — Ladas & Parry LLP

(57) ABSTRACT

A method for determining structures or geometry of an object, or for measuring an object using a CT measuring system, and for correcting projection data for a CT reconstruction with the application of a CT detector, wherein the CT measuring system includes at least one radiation source, at least one radiation detector, and at least one axis of rotation.

29 Claims, 17 Drawing Sheets

(56) References Cited

U.S. PATENT DOCUMENTS

Figure 1:
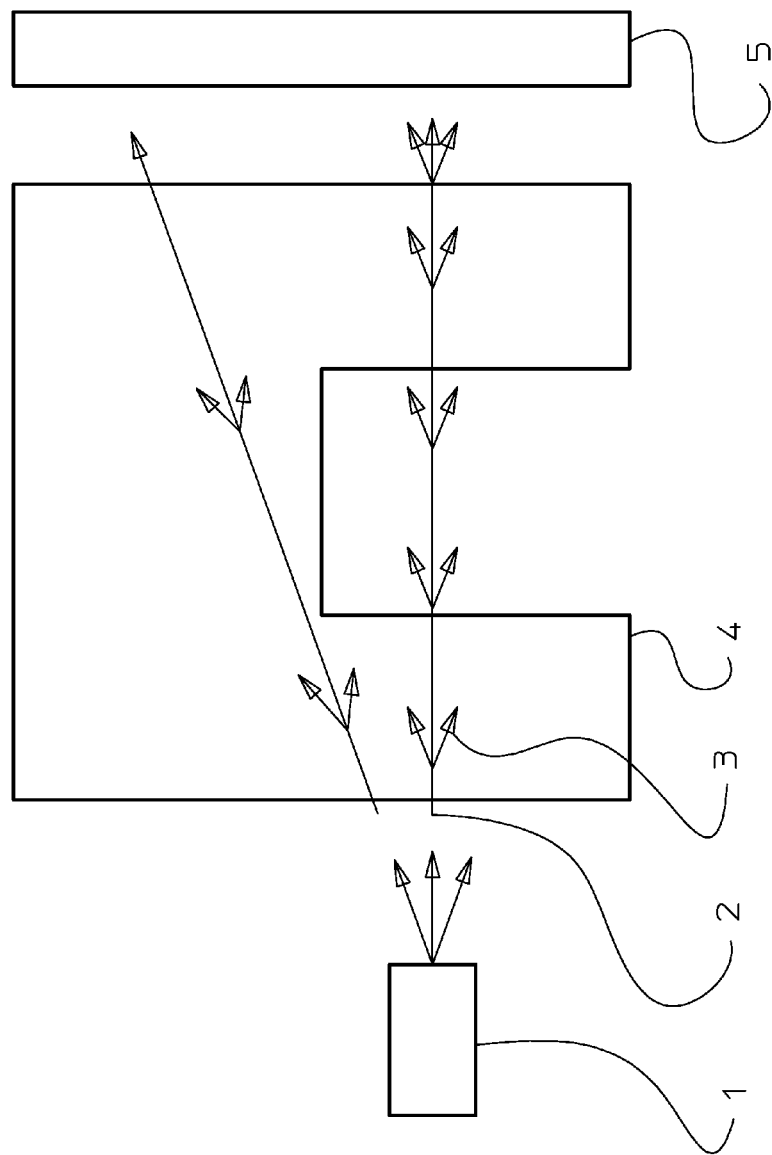

| | | | |
|---|---|---|---|
| 7,545,902 B2 | 6/2009 | Hoffman | 378/5 |
| 2005/0013404 A1 | 1/2005 | Kasperi et al. | 387/19 |
| 2005/0084147 A1 | 4/2005 | Groszmann | 382/131 |
| 2008/0075227 A1 | 3/2008 | Christoph et al. | 378/23 |
| 2008/0212734 A1 | 9/2008 | Kasperi et al. | 378/4 |
| 2010/0145653 A1 | 6/2010 | Christoph et al. | 702/152 |

FOREIGN PATENT DOCUMENTS

| | | | | |
|---|---|---|---|---|
| CN | 2666355 Y | | 12/2004 | A61B 6/03 |
| DE | 19542762 C2 | | 5/1997 | G01N 23/04 |
| DE | 10331419 A1 | | 1/2004 | G01N 23/06 |
| DE | 102005018447 A1 | | 10/2006 | G01B 15/00 |
| DE | 102008044437 | | 12/2009 | G01B 15/04 |
| WO | WO-2005/062856 A1 | * | 7/2003 | G01B 21/04 |
| WO | WO-2005/119174 A1 | * | 12/2005 | G01T 1/29 |
| WO | WO-2006/094493 A2 | * | 9/2006 | G01T 1/29 |
| WO | WO-2008/128978 A2 | * | 10/2008 | G01B 21/04 |
| WO | 2009132854 A1 | | 11/2009 | G01N 23/04 |

OTHER PUBLICATIONS

Chinese Search Report attached to Third Chinese Office Action dated Jun. 26, 2014, corresponding to Chinese Patent Application 201080008625.2.

Manfred Sindel et al. "Application of Computer Tomography (CT) on Aluminium Body Manufacturing at Audi AG", Giesserei Rundschau 53(2006).

Notice of Opposition against European patent 2399237 dated Jun. 24, 2014, corresponding to European Patent Application No. 10708956.7.

Chinese Search Report attached to The Second Chinese Office Action dated Nov. 11, 2013, corresponding to Chinese Patent Application 201080008625.2.

* cited by examiner

METHOD FOR MEASURING AN OBJECT

This application is a 371 of PCT/EP2010/052145 filed on Feb. 19, 2010, which is incorporated herein by reference.

The invention relates to a method for determining structures and/or geometry of an object or for measuring an object such as a workpiece by means of a measurement system, preferably a computed-tomography measurement system and for correcting projection data for a CT reconstruction with the application of a CT detector with pixels. In the CT measurement of a workpiece, this item is arranged on an axis of rotation between an X-ray source emitting X-radiation and an X-ray detector receiving X-radiation. The invention also refers to an arrangement for determining structures and/or geometry of an object by means of a measurement system, preferably a computed-tomography measurement system, consisting of at least one radiation source, at least one radiation detector, and at least one axis of rotation.

The use of computed tomography for measurement-engineering purposes can only occur with high accuracy when the reconstructed tomograms are free of artifacts, which are caused by various physical effects. These physical effects are, among other things, beam hardening, scatter, and also diffraction and refraction effects. For the correction of the artifact resulting therefrom, one characteristic line is calculated, at most, which takes into account the relationship between the transmitted length, as well as the geometry of the component, and attenuation values are measured with a detector.

EP 1415179 B1 describes a method whereby the transmission lengths from the artifact-bearing 3D voxel data of a sample which emerge from full projection data are measured iteratively. All the artifacts determined in the process are considered in the form of a beam-hardening correction. A single characteristic line is thereby determined from the measurement results of all the pixels of the detector.

A method is alternatively proposed in WO 2006/094493 (=EP 06722577.1), whereby the transmission lengths in the various rotation positions of the measurement object relative to the CT system of sensors are determined with the aid of a CAD model of the workpiece. Here, it is necessary to perform a precise alignment of the workpiece in the CT measurement system for the CAD data.

With the methods of prior art, however, it is not considered that not just the transmission lengths but the geometry of the workpiece as well, call forth different artifacts, particularly at the various rotation positions, due to different radiation scatter, for example. In addition, all the pixels of the detector are not taken into account through the correction with the aid of a single characteristic line for the projection data, so that artifacts are triggered by different properties of the individual pixels as well.

An object of the present invention is to develop a method of the type cited at the beginning such that an effective correction for artifacts results with CT measurements. According to the invention, the problem is essentially solved by the steps of claim 1, whereby different characteristic lines are used to correct the measurement values of the individual pixel or groups of pixels of the CT detectors used. According to the invention, the different measurement-engineering properties of the individual pixels are taken into account to determine the attenuation values of a detector used during transmission of the measurement object. According to the invention, several characteristic lines are determined for this, which describe the relationship between the transmitted component length and the attenuation value at the detector. Besides the transmission length, the geometry of the workpiece is additionally considered in the characteristic lines. This results, according to the invention, in the characteristic lines being adjusted to the transmission geometry at the various rotation positions of the measurement object, and therefore not only the transmission length, but the sequence of the various materials are considered in the transmission direction. The assignment of the characteristic lines to individual detector pixels occurs on the workpiece captured in the CT measurement system.

The determination of the geometry of the workpiece that is needed to define the characteristic correction lines can, for instance, be established iteratively from the full projection data or after alignment with CAD data, with the assistance thereof as already described in prior art.

The advantage of the approach being described lies in taking into account the different measurement-engineering properties of the individual pixels of the detector, but also the sophisticated consideration of beam hardening and radiation scatter, absorption in the component, and diffraction and refraction effects as well. Furthermore, the method also makes it possible to carry the individual characteristic lines along in a lateral movement of the measurement object perpendicular to the transmission direction (for example, in spiral tomography). At the same time, it is taken into consideration that the line integrals characterizing the radiation absorption along a transmission direction are defined at the various lateral positions by different pixels.

The consideration of artifacts due to radiation scatter, absorption, diffraction, and refraction effects can occur, for instance, by the characteristic lines comprising one or several parameters, which take into account the characteristic geometry (sequence of material) in the transmission direction at hand. This may, for example, be the weighted-average transmission lengths of the individual material segments or another contrast ratio imaged therefrom. Further analytical correction relationships can be determined with the aid simulations, for instance.

In particular, it is provided that the different measurement-engineering properties of individual pixels or groups of pixels and/or artifacts are established in computed-tomography imaging to determine the individual characteristic lines.

Measurement-engineering properties of individual pixels or groups of pixels represent the relationship between the efficiency of the beam being received and the sensor signal being emitted. This may vary for the individual pixel or groups of pixels, based on different offset values, and thus for sensor signals when irradiation is missing, and/or for different sensitivities.

At the same time, the effects due to artifacts are considered in the characteristic lines, wherein the transmission length assigned to individual pixels or groups of pixels and/or the geometry of the assigned workpiece is determined at the various rotation positions for recording various projection data during CT measurement.

Effects due to artifacts are taken into consideration in the characteristics lines such that each measured beam intensity I is not only assigned a single transmission length L, but a correction is recorded, depending on the first, roughly known transmission length and/or geometry of the workpiece, which makes it possible to determine the correct transmission length from the intensity measured. The recording can occur in the form of analytical descriptions or look-up tables.

In particular, it is provided that the determination of the transmission length and/or the geometry of the workpiece at the various rotation positions occurs using the current, nearly complete projection data and/or using a CAD model.

In an embodiment, the invention provides that the determination of the different measurement-engineering properties of the individual pixel or groups of pixel, particularly the sensitivity and the offset, occurs using the determination of transmission images, with and without measurement objects with known properties, especially the geometry.

Furthermore, it is provided, for correction of artifacts from the previously determined transmission lengths and/or the characteristic geometry present in the respective transmission direction, that one or several parameters are derived which are taken into consideration in the characteristic lines.

The parameters considered in the characteristic lines serve in adjusting to the characteristic geometry at hand in the respective transmission direction. With this, it should be considered that a given workpiece has different transmission directions at different rotation positions and because of that, the influence of characteristic lines imposed to correct artifacts occurs very differently.

Parameters can be derived from the characteristic geometry, wherein the line segments transmitted for each type of material and arrangement are determined from the geometry and/or sequence of materials and the formation of artifacts such as radiation scatter and beam hardening is inferred from this.

At the same time, the previously cited parameters can also take the sequence of materials into account. In particular, radiation scatter appears as increased if a more frequent exchange is present between different materials.

The possibility also exists of the parameters being derived from the characteristic geometry, wherein a weighted-average transmission length of the individual material segment or an otherwise analytically constructed contrast ratio is determined from the geometry and/or sequence of material, using simulations, for instance, and the formation of artifacts such as radiation scatter and beam hardening is inferred.

In order to analytically determine the number of the sequential materials, a contrast can be determined, for example, along the transmission direction. This will define the number of material changes. If the frequency of material changes at the transmission length at hand altogether is obtained, an inference can be drawn concerning the severity of the beam-intensity effect measured at the end of the transmitted length. In particular, radiation scatter is distributed, for example, over a greater width and causes smaller intensity changes for a pixel additionally impacted by radiation scatter, the greater the transmission length.

According to one embodiment, it is provided that different characteristic correction lines are determined and used, depending on the rotation position and/or the position of the workpiece.

The possibility also exists that the selection and assignment of respective characteristic lines to individual detector pixels and/or groups of pixels at the respective rotation positions or positions of the workpiece occurs through alignment with the workpiece.

In particular, it is provided that in the characteristic lines, the effects due to artifacts are considered, whereby, correction values, in common or different, are determined for the individual pixel or groups of pixels of the CT detector used, using at least one transmission image of the workpiece in at least one rotation position and/or workpiece position.

By comparing the transmission lengths determined from the individual intensities measured for individual pixels of the detectors (the transmission image) with the transmission lengths currently present and derivable from the geometry currently present, correction values can be determined for the individual pixel, as well as correction lengths. In particular, these correction lengths could be the same for adjacent pixels.

If the same transmission lengths are exhibited at other rotation positions of the measurement object in connection with the same sequences of material, then the correction values for the pixel affected can be partially assumed. However, possibly divergent physical or measurement-engineering properties of the pixel concerned must be taken into consideration.

At the same time, the measurement values of pixels of the CT detector are used to determine the correction, which are, for the most part, influenced by the portions of the X-ray radiation issuing from the radiation source, which does not proceed on a direct, straight-line path through the workpiece.

By measuring the intensity of the measurement beam not attenuated by the workpiece, variations in the intensity of the measurement beam are recorded, for instance, on the basis of fluctuations in the efficiency of the X-ray tube, and are used as a correction for all detector pixels, for example a gain correction.

The selection of pixels whose measurement values are used to determine the correction occurs by at least one transmission image of the workpiece being compared to at least one transmission image without the workpiece and using the comparison, all or a part of the pixels being selected which exhibit a higher measured intensity in the transmission image with the measurement object than in the transmission image without the measurement object. Or else the selection of pixels whose measurement values are used for correction occurs within the transmission image with the workpiece, wherein at least one pixel which is affected exclusively by portions of the X-ray radiation being emitted by the X-ray source and which does not proceed through the workpiece, is compared with at least one pixel being compared which exhibits a higher measured intensity.

At the same time, the possibility exists that the correction values determined using the selected pixels are used for the characteristic lines, all of whose pixels are uniform which receive X-ray radiation, which proceed on a direct path from the X-ray source through the workpiece, or that the correction occurs depending on the assigned transmission lengths of the individual pixels or groups of pixels and/or geometry and/or sequence of material of the workpiece at various rotation positions and/or workpiece positions.

The previously described comparison serves in the determination of the intensity of radiation scatter, which is valid for a certain area. This validity area is the area at the detector which contains those pixels that receive radiation, which proceed on a direct path through the measurement object. For all these pixels, a even superposition of radiation scatter is assumed, which is as a result uniformly corrected for all these pixels. If different transmission lengths or sequences of material are present within the validity area, then the corrections previously described and determined can still be adjusted accordingly.

In an embodiment, it is provided that measurement values of pixels that are used to determine the correction are determined and/or combined at one or several different workpiece positions between the X-ray source and the X-ray detector, in particular at various magnification settings, and are used at different magnification settings, by employing interpolation methods for instance.

The use of interpolation methods makes possible a correction for magnification in the characteristic lines, wherein the relationship between measured intensity and transmission length, as well as sequences of material would not be clearly dependent on the correction of the characteristic line.

For this, the corrections are used from the adjacent magnification settings are used, in particular lower and higher magnification settings.

Alternative or supplementary measurement values can be determined and/or combined for pixels that are used to determine the correction, in one or several different positions of the workpiece between the X-ray source and the X-ray detector and several different positions of the X-ray source relative to the X-ray detector, in particular with the same magnification settings but different beam cone-angles passing through the measurement object from the radiation emitted by the X-ray source, and are used at one or different magnification settings, for example using interpolation methods.

Just as explained previously, possibly different corrections appear necessary for different beam cone-angles. By determining these corrections at defined beam cone-angles using interpolation methods, these corrections are also extended to the beam cone-angles in between.

There also exists the possibility that by putting together a transmission image from several partial transmission images, whereby each of these transmits only a portion of the workpiece, through the use of filters, for example, the formation of artifacts, in particular radiation-scatter artifacts, is clearly reduced and by comparison with the fully recorded transmission image, the correction values are determined for at least a portion of the various pixels of the detector, and areas missing in the partial transmission images that are put together are interpolated and/or extrapolated as necessary between and/or at the irradiated area.

By using filters, the beam cone-angle is clearly reduced whose radiation is used for workpiece transmission.

Thus, the effect of artifacts, especially radiation scatter, can clearly be reduced. However a reduction in the measurement field accompanies this. Nevertheless, in order to measure the entire measurement object, it is necessary to put individual partial images together for the total transmission image.

At the same time, the total area of the workpiece does not inevitably have to be covered in the individual partial measurements. By comparing the same areas in the partial transmission image with the total transmission image, the altered effect of artifacts, especially radiation scatter, can be determined. This approach can be repeated for different partial transmission images that do not inevitably border immediately upon one another. By interpolating the correction values of these partial transmission images, the correction can also be determined for the areas between these partial transmission images by means of interpolation.

It is also possible, as well, to determine the correction values for areas outside the partial transmission images by means of extrapolation.

An embodiment of the invention provides that different characteristic correction lines are determined and used to make raster methods possible, depending on the rotation position of the workpiece and/or the position of the workpiece, wherein the position of the workpiece between the X-ray source and the X-ray detector can be changed in the direction of the principal beam axis of X-ray radiation and/or at right angles to it.

If the tomography takes place at different positions of the workpiece within the measurement volume, then a specified area of the measurement object is only imaged at one other pixel. In order take into consideration possibly different measurement-engineering properties of this pixel during correction, the artifact correction determined for the original pixel can transfer the characteristic line to the pixel now in question and can be transferred with the correction correcting the divergent measurement-engineering properties.

The selection and assignment of the respective characteristic lines for the individual detector pixel and/or groups of pixel can occur in the respective rotation positions or positions of the workpiece by alignment with the workpiece.

There also exists the possibility that different characteristic lines are determined and used, depending on the spectrum used for the radiation passing through the measurement object, preferably by using different beam voltages for the X-ray tube and/or by using prefilters.

When using different spectra for the radiation passing through the measurement object, the artifacts, beam hardening in particular, but also radiation scatter, are expressed differently. Thus, different characteristic correction lines must be derived.

According to a further proposal, it is provided that the correction of the characteristic lines of an individual pixel or group of pixels for the radiation detector occurs during the recording of the various transmission images at the various rotation positions and/or positions of the workpiece or after recording the full set of transmission images.

In particular, it is provided that CT reconstruction occurs for a CT measurement system which is part of a coordinate-measuring device.

A further premise in using computed tomography for measurement-engineering purposes with high accuracy is that the transmission images serving for reconstruction at the various rotation positions of the workpiece can be unambiguously assigned spatially to one another. This is however inevitably due to wobbling motions during the rotation of the measurement object or shifts between the X-ray tube, in particular the focus of the X-ray tube, and it impedes the X-ray detector. The size of the two effects can be reduced by a particularly stable construction, thermally as well as mechanically, of the individual components. Furthermore, highly precise axes of rotation are used for rotating the measurement object, that is, wobbling motions that appear are determined and corrected. Among other things, by heating the X-ray tube, drift movements of the X-ray tube focus that appear are temporarily reduced, whereby one must wait for a corresponding heat-up, and because of that warm-up, of the CT system. Furthermore, methods are known in which an additional, permanently arranged measurement body is introduced into the X-ray radiation path, using whose image the focal-point drift can be corrected at the CT detector.

The basis of a further aspect of the present invention is the object of developing a method of the type mentioned in the beginning so that the projection data can be corrected at little measurement-engineering expense and basically without using a calibration body.

To solve this problem, the invention provides essentially that during the measurement run, the relative measurement motion occurring between the X-ray source and the X-ray detector is corrected by means of information previously obtained.

At the same time, it is particularly provided that a transmission image of the workpiece to be measured or several transmission images of the workpiece to be measured are recorded as pre-information at various rotation positions and/or different workpiece positions relative to the X-ray source and/or the X-ray detector.

According to the invention, a correction occurs using a clearly smaller number of pre-recorded transmission images than for transmission images used directly for measurement on the same measurement object.

A method is proposed for correction, during the CT measurement, of shifts occurring between the X-ray source or the focus of the X-ray source and the X-ray detector or the workpiece. For this, one or several pre-transmission images are first recorded for the workpiece or parts of the workpiece, such as, by way of example, individual features. In order to minimize drift phenomena in the pre-recording, only a few little transmission images are recorded in a few different rotation positions. By comparing the pre-recorded transmission images or portions thereof and the transmission images recorded during the measurement or parts thereof, a shift or scaling discrepancies can be recognized, for example with the aid of correlation methods, and be corrected. This can occur, for instance, by means of resampling methods or positioning of the X-ray source relative to the X-ray detector and/or the workpiece. The transmission images used for measurement for which no pretransmission images exist are corrected with the aid of interpolation methods from the pre-recorded transmission images of adjacent rotation positions of the workpiece.

The advantage of the approach described lies in saving additional transmission bodies from being permanently introduced to determine focal drift, as these drift bodies also underlie drift phenomena during measurement and furthermore can restrict the measurement area of the CT system. On the basis of the small number of pre-recorded transmission images for correcting transmission images determined during actual measurement, a very short measurement time occurs with pre-recording, whereby focal drift phenomena are minimized. In comparison with actual measurement, in which about 100-1600 transmission images are distributed over a full or half-circle, pre-transmission images are only recorded if necessary in irregularly distributed increments of about 5 to 20 degrees. A correction for drift can also be made as well, using an individual transmission image, wherein at the beginning and end, as well as for any further arbitrary point in time during the measurement, a transmission image is repeatedly determined for this position.

Hence, it is particularly provided that the number of pre-recorded transmission images is clearly less, typically 20 to 70, than the number of transmission images required for the measurement, typically 100 to 1600.

In an embodiment of the invention, it is provided that the correction occurs using a pre-recorded transmission image, wherein a repeat measurement of the workpiece to be measured occurs at one or several desired, selectable points in time during the measurement run at the rotation position and workpiece position at which the pre-recording was determined.

The invention is also distinguished by the determination of correction data occurring for the individual transmission images used for measurement by comparison with the pre-recorded transmission images, for example with the aid of correlation methods, and shift and/or scaling based on the comparison, preferably by means of re-sampling methods, of individual transmission images used for measurement, parts of these transmission images, or one or several features within these transmission images.

There also exists the possibility that transmission images for which no pre-recorded transmission image exists at the same rotation position of the workpiece are corrected, the information from the pre-recorded transmission images being used that was recorded at adjacent rotation positions, preferably using interpolation methods.

In an embodiment of the invention, it is provided that the shift and/or scaling based on comparison of the pre-determined transmission images and the transmission images used for measurement are used to correct the relative position between the X-ray source and/or the X-ray detector and/or the workpiece during the measurement run by means of positioning.

In particular, it is provided that the correction method for a CT measurement system finds application in being part of a coordinate-measuring device. Here, in particular, a multisensor coordinate-measuring device is involved.

As already mentioned, distortion of the signals recorded arises when recording transmission images for X-ray tomography, due to different effects such as radiation scatter or beam hardening. This leads, in particular, to measurement discrepancies that exceed the allowable range when using X-ray tomography for measurement-engineering purposes. To correct such discrepancies, various methods are known from the literature, which have already been mentioned in part.

In EP-A-1 415 179, a method is described for iterative correction of corresponding error effects, also called artifacts. Thus first of all, a first rough reconstruction is produced from the still distorted transmission image. From this, lengths are calculated with which a characteristic correction line for the transmission images is executed. Then an exact reconstruction of the measurement results.

The object of WO-A-2006/094493 is a method in which the additional nominal data such as CAD data are taken into consideration in determining beam-hardening artifacts.

Similar methods are described in the dissertation of Michael Maisl, "Development and Construction of a High-Resolution X-Ray Computed-Tomography System for Workpiece Examination" from 1992.

Also known are methods according to which additional measurements are made with other sensors on the same workpiece. On this basis, the measurement points produced can be corrected geometrically at their location, with the aid of transmission-image recording and subsequent reconstruction. As an example, EP-A-1 749 190 and WO-A-2008/128978A2 may be referred to.

In both of the first-cited methods, the disadvantage exists that no restorable measurement results are cited when determining the correction values. The accuracy achievable is thereby severely limited. The disadvantage of the last-cited method consists of all the surfaces needed for later evaluation having to be additionally measured individually, at least with a pattern workpiece. A considerable measurement expense arises thereby, which limits the use, on economic grounds, to only a few features to be measured with high accuracy.

A further object of the present invention is, for one thing, to avoid the disadvantages of the methods cited above and for another thing to achieve a considerable improvement in the accuracy of the targeted reconstruction results.

According to the invention, the problem is essentially solved by a correction in the transmission images occurring whereby the transmission images are subjected to a characteristic-line correction, in which calibrated lengths obtained by means of calibration measurements on the same workpiece are taken into consideration.

It is particularly provided as well that the measurements for the calibration of the calibrated lengths are executed with the aid of a coordinate-measuring device.

Preferably, the measurements for determining the calibrated lengths are made by means of multisensor coordinate-measurement equipment, into which a sensor system is integrated for X-ray computed tomography.

In particular, it is provided that only a few of the transmission lengths evaluated by X-ray tomography, typically 10 to about 100 transmission lengths, are calibrated to determine the characteristic correction lines.

An especially preferred embodiment of the invention provides that the transmission images evaluated to determine the characteristic correction lines are, insofar as possible, distributed from 0 up to the maximum occurring transmission length of the corresponding workpiece. At the same time, the transmission lengths evaluated from determining the characteristic correction lines at different rotation positions for the workpiece can be determined on a computed-tomography beam path.

Specific to the invention, it is proposed that the characteristic correction lines be determined by comparison between the characteristic line representing the relationship between the transmission length and the measured beam intensity and the measured beam intensity assigned, with the aid of calibration measurements of the transmission lengths determined.

The invention is also distinguished in particular by the determination of the characteristic correction lines occurring by interpolating the transmission lengths and accompanying transmission values between the calibrated values and/or by extrapolating above and/or below the calibrated values.

What is more, spline interpolation, polygon interpolation, or interpolation with functions with an analytical description can preferably be used as interpolation methods.

Preferably, recording the characteristic correction lines should occur using analytic functions and/or discrete value tables (look-up tables).

Specific to the invention, it is provided that the determination of the calibrated lengths occur preferably by means of optical or tactile measurements of the entry and exit points of a portion of the incident radiation (beam) at the workpiece and/or by determining the entry and exit point by means of a mathematical combination of preferably optically or tactilely measured compensation elements, preferably planes or cylinders, in the area of the respective points of intersection through the workpiece surface.

In particular, the alignment of the workpiece should occur using the measured geometric control elements and/or by adjusting parts of the workpiece and/or the total workpiece.

The solution to the problem lying at the basis of this invention can essentially be achieved by individual typical lengths being precisely measured on the workpiece to be measured, by means of an additional measurement with a coordinate-measuring device or with additional sensors integrated into the coordinate-measuring device with computed tomography. These different, individual, "thus calibrated" lengths correspond, when using computed tomography, to transmission lengths that appear (at the line connecting the X-ray source and the sensor element). From the corresponding 2D transmission images and a first rough reconstruction of all the transmission lengths, characteristic lines can be produced with the aid of the calibrated transmission lengths for correcting the 2D transmission images, which describe the relationship between the attenuation values determined from the sensor signals of the 2D transmission images, for example in the form of grey values, and the component lengths transmitted. The accuracy of this characteristic-line calculation is defined by the accuracy of the calibration measurement for the transmission lengths selected.

The calibration of the corresponding transmission lengths can occur in principle in two ways. For one thing, it is possible to directly contact, optically or tactilely the intended entry and exit points of the corresponding beam at the workpiece. Alternatively, it is likewise conceivable to measure compensation elements in the area of the respective points of intersection through the workpiece surface, for example planes or cylinders, and to determine the points of intersection therefrom by mathematical combination.

In order to find the corresponding points exactly, in both the reconstructed volumes and with optical or tactile counter-measurement, for example, at the workpiece, it is reasonable to perform a prior workpiece alignment mathematically. This can alternatively occur by alignment with measured geometric control elements or by adjusting parts of the workpiece or adjusting the entire workpiece.

In carrying out the method, it is reasonable to use a decent number of 10-100 transmission lengths, for example, with lengths as uniformly distributed as possible between 0 and the maximum length. For this, it is likewise reasonable to determine the corresponding measurements from different rotation positions of the workpiece in the computed-tomography beam path. The determination of the characteristic lines for correcting the transmission images then occurs by interpolating the corresponding lengths and accompanying transmission values between the calibrated values. Various known methods, such as spline interpolation, polygon interpolation, or interpolation with functions with analytical description occur as interpretation methods.

In order to make dimensional measurements on components with the aid of measuring equipment using computed tomography sensors, it is necessary to execute several settings for the X-ray source and for the X-ray detector used, such as the axis of rotation used to rotate the component. This particularly concerns the current and the beam voltage of the X-ray tube, the exposure time for each transmission image, the number of image averagings over several transmission images, the number of averagings over adjacent pixels of the X-ray detector (binning), the magnification selected (position of the workpiece between X-ray source and X-ray detector), and the number of rotation positions for the workpiece at which the transmission images are recorded. Depending on the maximum transmission length and the geometry of the component, as well as the voxel resolution and accuracy to be achieved, these parameters have to be expensively prepared by hand. At the same time, care has to be taken in particular, as a result, lest the pixels at the X-ray detector be overradiated or appear too dark at any of the rotation positions. In addition, optimal results can be attained, wherein the contrast of the detector images is as high as possible, as well as the grey-value difference between the brightest and darkest pixels used for evaluation.

The present invention is, for that reason, also based on the object of selecting the parameters needed for computed tomography (CT) so that as high a quality as possible is attained, such as contrast-rich imaging at a detector, especially independent of the rotation position of a workpiece to be measured, that is, at rotation positions alone.

To solve the problem, the invention provides, in particular, that parameters for the computed tomography are selected using pre-recorded transmission images.

What is more, it is specific to the invention to provide that the parameters to be used for the computed tomography are determined from the pre-transmitted images by means of mathematical methods or by variations in the parameters.

One strength according to the invention is offered by the selection of the parameters to be varied and/or the area of variation being fixed and/or determined by the operator and/or using at least one transmission image.

It is stressed that it is provided that the current and/or the beam voltage of the X-ray source and/or the exposure time at the detector and/or the number of averagings per transmission image and/or the number of averagings over pixels of the detector (binning) and/or the number of rotation positions of the measurement object between the X-ray source and the X-ray detector and/or the position of the object between the X-ray source and the X-ray detector (magnification) is or are selected as the parameter for computed tomography.

The proposal also has the typical character that at least one of the parameters is varied automatically, up to an output quantity, preferably the contrast in the transmission image, so long as it assumes a maximum and/or exceeds or does not meet a pre-defined value.

It is furthermore emphasized that valid values of the contrast of the difference between a grey value of the brightest and of the darkest pixel of at least one part of the total transmission image correspond per transmission image and/or over all the transmission images, while the darkest detector pixel has a grey value greater than a pre-defined minimum and the brightest pixel has a grey value less than a pre-defined maximum.

Independent of this, it is provided in particular that the teaching according to the invention is realized in measuring with a coordinate-measuring device, i.e. that the computed tomography measurement system is part of a coordinate measurement device.

It is provided according to the invention that an optimum for a control quantity such as image contrast is attained, using a few pre-recorded transmission images in different rotation positions and when varying one or several parameters such the current and/or beam voltage of the X-ray tube and/or exposure time at the detector and thus image brightness and/or number of image averagings as well as number of pixels being put together (binning) and/or magnification and number of rotation steps, in order to first use one of these parameter then for the computed tomography (CT).

A method is proposed according to the invention for automatic determination of at least one parameter for computed tomography, whereby one or several parameters are selected for computed tomography, using a pre-recorded transmission image.

The advantage of the invention consists of the fact that the adjustment of the optimal CT parameters can automatically occur and thus, on the one hand, the preparation time for a CT can be shortened and on the other hand, error judgments by the operator can be reduced.

In particular, the invention provides that the maximum contrast is attained when the difference of grey values for the brightest and darkest pixels at the detector is as great as possible, whereby at the same time the grey value of the darkest pixel is greater than a minimum value and the grey value of the brightest pixel is less than a maximum value. The transmission images to be recorded for this should clearly be fewer in one manifestation of the invention than the number of transmission images for the measurement proper. The pre-recorded rotation positions must be selected so that the minimum and maximum transmission lengths of the component are included. It is thereby ensured that the brightest pixel is not overradiated and the darkest pixel does not appear too dark.

With measurement systems known to date, preferably computed tomography measurement systems using axes of rotation, it is necessary that the workpiece, such as a rotationally symmetric workpiece, be placed in alignment with a physical axis of rotation in order to achieve measurement results of high accuracy. In computed-tomography imaging, it must be ensured, moreover, that the axis about which the workpiece is rotated remain aligned at all rotation positions relative to the detector in order to make a reconstruction possible. In order to align the measurement object with the axis of rotation, a time-intensive adjustment is necessary.

A corresponding arrangement for adjusting the workpiece in the center of the axis of rotation is already known as a measuring device of the Primär series from the company of Mahr, Göttingen. The resultant lateral motion of the workpiece otherwise ensures, during rotation, especially for very small parts which preferably are measured at tomographically or optically high magnification, that the workpiece is not fully imaged at the detector in all rotation positions. This is, however, a prerequisite for a measurement that can be evaluated. In the same way, the use of fast set-up and adjustment times, for example to hook-up to automated equipment, is required on the production line.

Disadvantageously moreover, in methods known to date for computed-tomography measurement, parts which possess clearly different dimensions cannot be imaged in all rotation positions with sufficient contrast at the same beam energy. The cause of this is the different transmission lengths that appear and the attenuation of the measurement radiation associated therewith. The radiation reaching the detector then only delivers information that can be evaluated if all areas (pixels) of the line or surface detector involve intensities above a minimum and below a maximum value. In order for all rotation positions to obtain this so-called evaluatable contrast in the transmission images with the same beam energy, the differences in the beam attenuation along the transmission length must not exceed a specified value in the smallest and second largest dimension of the workpiece. The largest workpiece dimension is for the most part preferably arranged perpendicular to the transmission direction, insofar as the measurement volume allows it.

Workpieces which are very extensive in two dimensions and are very short in the third can currently only be measured using at least two measurements with different beam energies. What is more, a respective full measurement is made in all rotation positions from 0° to 360° with at least two different beam energies. Then, for each rotation position, a transmission image is calculated from the at least two transmission images of the individual measurements. This data fusion involves an adjustment of the respective transmission images put together for each rotation position. These images naturally contain overradiated or too-dark areas, as well as areas without contrast that are evaluatable. Accordingly, they must not be used for evaluation and they are replaced by information from respectively at least one of the other transmission images for this rotation position. In order to ensure absolute coverage of the image intensity, an adjustment or normalization of the accompanying images occurs in advance at the same intensity level, preferably using the intensities from the areas of the transmission images which are at the same time either overradiated or too dark in all the images. This is possible, for instance, by so-called "downscaling", "upscaling", or by averaging and in the same way represents a component of the present invention in connection with the method according to the invention.

For the combined evaluation of measurement values from computed tomography measurements that result at different positions of the same workpiece, only methods are known from prior art to date in which measurements are made at the same magnifications and thus almost the same pixel or voxel rasters set next to one another. A corresponding approach is described in WO-A-2005/119174. The ordering of the measurement data to one another then occurs by taking into consideration the relative positions between the measurement object, radiation source, and detector, which preferably proceed through the exact axes of motion of a coordinate-measuring device or by stitching methods. However, as a result, the combined evaluation of measurement data is not resolved, which would be determined from measurements at different magnifications. What is more, divergent pixel or voxel rasters must be taken into consideration. The combined evaluation of measurement values at different magnifications is necessary in order to determine very accurately, for instance, small details of a workpiece at high magnification and to be able to nevertheless determine the position of the details in the total volume if at lower accuracy as well, due to the lower magnification and thereby resolution necessary for this.

In particular, it is not, moreover, resolved that parts of the measurement object that are perpendicular to the axis of rotation in at least a few rotation positions depart from the measurement volume with tomographic measurement at high magnifications. Transmission values missing for those parts not imaged which are perpendicular to the axis of rotation at the detector prevent the reconstruction of volumetric data for the workpiece. In contrast thereto, only methods of prior art are to be inferred in which the parts of the workpiece that are not imaged are located exclusively in the direction of the axis of rotation.

The task at the base of the present invention is also to avoid the disadvantages of prior art and to be able, in principle, to measure workpieces with different dimensions with high accuracy while avoiding expensive correction methods, in particular avoiding the problems of workpiece alignment.

The present invention solves the problem, in particular the problems of workpiece alignment by measurement results, particularly recordings with an image-processing sensor or transmission images which are determined at different rotation positions of the workpiece, by the combination of translational and rotational movements being precisely combined directly, without previous alignment of the workpiece with the physical axis of rotation being necessary. The basic idea moreover is that the measurement object is rotated about a virtual axis of rotation which need not inevitably coincide with the physical axis of rotation and the physical axis of rotation is moved on one or two axes and if necessary the detector is moved on at least one axis while rotating the physical axis of rotation. By rotating the workpiece about a virtual axis of rotation, preferably an axis of symmetry of the workpiece, it is achieved that the workpiece is always imaged independently of the current rotation position at approximately the same detector position. Lateral movement of the workpiece relative to the detector is avoided by means of the following two possibilities.

A first possibility involves the detector remaining motionless, but the measurement object rotating about a fixed axis of rotation relative to the detector. This is then also particularly possible if the workpiece is not arranged aligned with the physical axis of rotation. This is achieved wherein the physical axis of rotation on which the workpiece is arranged as fixed, is positioned in two directions respectively so that the workpiece rotates about a virtual axis of rotation in space. The physical axis of rotation moreover moves during its rotation on a circular path about the virtual axis of rotation, though only additionally by means of both translational movements. The translational movement results, for example, by means of a mechanical stage that exhibits two translational degrees of freedom.

A second possibility involves the selective readjustment of the detector in combination with at least one translational movement of the axis of rotation. The detector is readjusted to the virtual axis of rotation, which only moves in one direction during the rotation of the physical axis of rotation, in this one direction. This direction is perpendicular to the physical axis of rotation and perpendicular to the normal to the plane of the detector. In the direction of the normal to the plane of the detector, the virtual axis of rotation, however, is also fixed when the measurement object is not arranged aligned with the physical axis of rotation. This is achieved wherein the physical axis of rotation is readjusted accordingly in the direction of the normal to the plane of the detector. What is more, the physical axis of rotation executes a linear motion in order for the distance between the virtual axis of rotation and the plane of the detector to remain constant in the direction of the normal to the plane of the detector. The lateral motion of the virtual axis of rotation and of the detector leads in the imaging beam to the same areas of the workpiece only being imaged with changed angles for the imaging beam. The measurement deviations resulting at the same time can be corrected by means of mathematical methods and if necessary a return of the detector in a direction running parallel to the axis of rotation. The corresponding methods have already been described in DE-A-10 2008 044 437. A premise for using the correction is that a rotation center stop and the magnification, as well as the position of the imaging beam, axis of rotation, and detector are known in common. EP 05750966.3 describes the method needed for the determination.

In order to fulfill the condition that the axis about which the workpiece is rotated and which is also the virtual axis of rotation remain arranged at all rotation positions aligned relative to the detector, this physical axis of rotation is shifted in the first step after arranging the workpiece on the physical axis of rotation, using at least one translational movement so that the virtual axis of rotation is aligned with the detector. Corresponding alignments, for instance with transition measurements can be gathered from prior art, EP 05750966.3, for example. Preferably, this alignment can be fast and accurate if high-precision axes of a coordinate-measuring device, preferably computer numerical control (CNC) axes, are used.

A control computer is used to control the combination of translational and rotational movements. For this, the relative location between the virtual axis of rotation and the physical axis of rotation must moreover be known. This location is either known from the method already described for aligning the workpiece or is determined, wherein control measurements made in advance at different rotation positions of the physical axis of rotation, preferably transmission images, are extended. DE-A-10 2008 044 437 and EP 05750966.3 describe the methods needed for this. These methods can occur in the same way during the measurements proper between the measurements in the various rotation positions. If further sensors are available on the device, these can be used in advance or during the measurement to determine the relative location between the virtual axis of rotation and physical axis of rotation.

Transmission images for the measurement proper are preferably only recorded when pre-defined angles about the virtual axis of rotation are reached. A constant angular raster and the conventional reconstruction of the measurement volume are thereby made possible. The control computer used for this recognizes when the respective rotation position and lateral position are reached, with the aid of a combination of translational and rotational motions.

Preferably rotationally symmetric parts and/or tools and/or tomography-capable parts are used as workpieces.

In a further aspect of the invention, the measurement of parts with clearly different dimensions that cannot be imaged in all rotation positions in sufficient contrast with the same beam energy are simplified. Fewer measurements are needed for this than in prior art, since a recording at each beam energy is not needed for each rotation position.

According to the invention, the beam energy and/or the wavelength region used, preferably the tube beam-voltage, the tube current, and/or wavelength-limiting filters, is adjusted to the respective geometry in question, preferably the transmission length and/or the material in question, preferably the material density. As a result, there is not an image for each rotation position with all beam energies. A faster measurement results by preferably for the measurement with, for example, two beam energies at each rotation position, only one image being recorded with either one or the other beam energy. For the later data fusion, it may possibly be necessary to record images, at least for a few rotation positions, at more than one beam energy.

The selection of the beam energy to be used for each rotation position occurs using a few pre-recorded transmission images and/or using the images recorded during the measurement proper in one or several previous rotation positions and/or using the geometry and/or material data known in advance, preferably from the CAD model of the workpiece. With pre-recordings, a data set with suitable beam energies can be preferably automatically determined at a few rotation positions by varying the recording parameters such as the beam energy. The beam energies are interpolated for the missing rotation positions. This is possible since it is not to be calculated with erratic changes in transmission length or materials from rotation position to rotation position. In the same way and for that reason as well, the parameters are determined for the current rotation position from the parameters of the previous or several previous rotation positions of the measurement run itself and which describe the beam energy, preferably by averaging or extrapolation. By means of monitoring, permanent or resulting first of all after several rotation positions, for the image parameters for the transmission images recorded, preferably by analysis of maximum intensity exceeded and of minimum intensity not attained, the adjustment of beam energy then occurs for the respective current rotation position. Furthermore or alternatively, existing information on the geometry at one's disposal can be used in advance, and therewith after registering existing transmission lengths for the individual rotation positions at one's disposal, and/or the material of the workpiece, in order to fix the beam energies to be used for each or for individual rotation positions. Intermediate values can in addition be interpolated. From the workpiece data, the beam energies needed for the respective rotation positions can be determined with the aid of image simulation, preferably by simulating the beam attenuation, the scatter, and/or the detector sensitivity; as a result the transmission images contain a contrast that can be evaluated.

In order to make possible the adjustment already in prior art or normalization of the accompanying images recorded at different beam energies at the same intensity level, there is a virtual creation of the transmission images with the beam energies with which it would not be possible to measure by interpolation. As the basis for this, transmission images determined for the same beam energies are used, preferably at adjacent rotation positions. Furthermore, adjustment is possible by comparing the radiation parameters used. Using selected accompanying image pairs for this at same rotation position but different beam energies, transformation equations are determined for this, which preferably are used for images of similar beam energies and/or similar intensity distributions present at the detector. Missing transformation equations for further beam energies or intensity distributions are interpolated in addition.

The present invention resolves the combined evaluation of measurement values for computed-tomography measurements, which would be recorded at different sites and/or at different magnifications and therefore pixel or voxel rasters, by merging and/or re-sampling of the reconstructed volumetric data of the different measurements. The individual measurements can at the same time be spatially superimposed, whereby the reconstruction values, particularly grey values, are determined in the weighted overlapping areas. The weighting occurs, for example, as a function of the distance to the overlapping boundaries. Re-sampling on a standardized three-dimensional raster is necessary in order to make possible the subsequent use of volume filters at the combined measurement-data set put together.

If details for a workpiece are determined at high magnification, then possibly parts of the workpiece may not be imaged at the detector at a few rotation positions. If these unimaged parts are laterally in a direction perpendicular to physical and/or virtual axes of rotation outside of the measurement area, then the areas in the transmission images that are missing from the measurement values, preferably in the transmission images of the same respective rotation angle, are calculated for at least one measurement with a lower magnification, at which the corresponding part of the workpiece was imaged at the detector. The calculation of the respective transmission value preferably occurs with re-sampling methods and/or interpolation methods and/or extrapolation methods.

A prerequisite for the combined evaluation of several data sets of volumetric data, in particular grey values, is precise assignability in space. The motion of the components to change the measurement segment of the workpiece and to change the magnification, as well as the axis of rotation bearing the workpiece, the X-ray source, and the detector hence occurs with precise coordinate measuring-device axes. In contrast to stitching methods, thereby no overlapping areas have inevitably to exist.

In the re-sampling of volumetric data, the various data sets are first arranged in space according to their recording position. For this, there exists an X, Y, and Z position for each grey value. Then a fixed X, Y, Z raster is established for all data sets for which the accompanying grey value was interpolated. What is more, a standardized data set that can be represented and evaluated is produced. It is possible first of all to thereby determine the gaps between high-resolution features and to use volume-based filters.

Preferably, the method or methods are used in a coordinate-measuring device and/or the arrangement is integrated into a coordinate-measuring device.

The invention is distinguished by the following, among other things, by structures and/or geometry of an object such as a workpiece by means of a measurement system, preferably a computed-tomography measurement system, including at least one radiation source, at least one radiation detector, and at least one axis of rotation, by recordings, preferably transmission images originating from different rotation positions of the workpiece being combined, for which:

the workpiece, with the aid of relative translational and rotational motions between workpiece and detector, is rotated about an axis of rotation different from the physical axis of rotation, and/or different beam energies are used and/or the measurement object, radiation source, and/or detector occupy several positions relative to one another. At the same time, it is provided, in particular, that the workpiece, with the aid of a combination of rotational and translational motions, is rotated about an axis of rotation different from the physical axis of rotation, whereby the physical axis of rotation relative to the detector and/or the radiation source is not fixed, wherein the physical axis of rotation is moved in at least one translational direction and/or the detector is moved in at least one translational direction and/or at least one rotational direction or that the workpiece, with the aid of a combination of rotational and translational motions, is rotated about an axis of rotation different from the physical axis of rotation, in which the detector is fixed and the physical axis of rotation is moved in two translational directions, whereby the first direction runs nearly perpendicular to the plane of the detector and the second direction is nearly perpendicular to the direction of the physical axis of rotation and runs nearly perpendicular to the normal of the plane of the detector.

Specific to the invention, it is proposed that the workpiece be rotated about a non-fixed physical axis of rotation relative to the detector and/or the radiation source, in which the physical axis of rotation is moved in a translational direction that runs almost perpendicular to the plane of the detector, and the detector is moved in a direction running in the plane of the detector, which is perpendicular to the direction of the physical axis of rotation and preferably the detector is rotated about a direction that is almost parallel to the physical axis of rotation and/or the measurement results are corrected, taking into consideration the transmission of a workpiece that is off-center relative to the illumination and/or the current rotation of the detector relative to the illumination.

Independent thereof, the axis of rotation differing from the physical axis of rotation can be the virtual axis of rotation of the workpiece, preferably an axis of symmetry.

Preferentially, the physical axis of rotation moves on a smooth, closed curve such as an elliptical path, especially a circular path, about the virtual axis of rotation or on a straight line that preferably runs perpendicular to the plane of the detector.

Using the teaching according to the invention, structures, and/or geometries of rotationally symmetric parts and/or tools and/or tomography-capable parts can be determined.

The idea enjoys independent protection that a measurement occurs without priors alignment of the workpiece to the physical axis of rotation and during the rotational motion of the physical axis of rotation, a translational motion occurs of the physical axis of rotation and/or of the detector, whereby the virtual axis of rotation, by means of a resultant alignment before and/or during the measurement proper, preferably with the aid of a CNC-controlled coordinate axis, always remains arranged aligned with the detector.

It is also according to the invention that a control computer determines the relative position of the virtual axis of rotation for a physical axis of rotation in space and therewith controls the combination of translational and rotational motions, wherein
  in at least two rotation positions of the physical axis of rotation adopted at the different rotation positions, control measurements are recorded in advance or between the measurements proper, preferably transmission images, from which the respective position of the virtual axis of rotation is determined for the physical axis of rotation or for a position of the body characterizing the physical axis of rotation, such as, for example, a cylinder or dome, in at least one coordinate and the results of the control measurements are combined, and/or
  the position of the virtual axis of rotation is determined for a physical axis of rotation by means of a further sensor system integrated into the equipment prior to or during the measurement.

Preferentially, transmission images are respectively recorded only when predefined angles about the virtual axis of rotation are reached.

Likewise, the possibility is offered that recordings, preferably of transmission images, are recorded for the various rotation positions with different beam energies, whereby recordings with all the beam energies used do not occur for each rotation position.

There exists the possibility that different beam energies are produced by changing the beam voltage and/or the tube current of the source producing radiation, preferably an X-ray tube, and/or varying the radiation filters used.

It is also provided that the respective beam energies applied are selected as a function of the current maximally available and/or minimally available transmission length at the respective rotation position and/or of workpiece material.

Specific to the invention, it is taught that the beam energies to be applied for at least a few rotation positions
  are determined from a few pre-recorded transmission images, in which parameters are set preferably automatically in advance which trigger a contrast that can be evaluated at the detector, whereby almost all the elements of the detector exhibit intensities greater than a minimum value and less than a maximum value and for all further rotation positions the beam energies are interpolated and/or
  are determined using the images recorded during the measurement proper in one or several of the previous rotation positions, preferably by averaging and/or extrapolation and/or
  are determined by the monitoring, permanently or resulting first of all after several rotation positions, of the image parameters of the transmission images recorded, preferably by analysis of maximum intensity exceeded and minimum intensity not attained and/or
  are determined using previously known geometry and/or material data such as density, preferably from the CAD model of the workpiece and preferably by interpolating for missing rotation positions and/or
  are determined from workpiece data with the aid of image simulation, preferably by simulating the beam attenuation, scatter, and/or detector sensitivity.

Detached therefrom, it can be provided that a fusion occurs of the transmission images produced with the aid of different beam energies by adjustment at the same beam-intensity level, wherein
  the transmission images are produced virtually with the beam energies for which there was no measurement, by interpolating from transmission images of the same beam energy determined at adjacent rotation positions, and/or
  a transformation occurs using the ratios of beam parameters used, and/or
  transformation equations are determined using selected, accompanying image pairs of the same rotation position but different beam energies, which are preferably used for images of similar beam energy and/or similar intensity distributions currently at the detector and preferably missing transformation equations are interpolated for further beam energies or intensity distributions.

The possibility exists that the transmission images recorded at the several relative positions between the measurement object, radiation source, and/or detector, preferably at different magnifications are first reconstructed for each combination of relative positions for a volumetric data set, whereby these can partially overlap, to be subsequently represented in space in a common raster and can be evaluated.

Preferentially, in at least one of several relative positions between the measurement object, radiation source, and/or detector, preferably at higher magnification, a part of the workpiece is not fully imaged at the detector in at least one rotation position, whereby this part of the workpiece perpendicular to the virtual axis of rotation departs from the accessible measurement area, and the measurement values in the transmission images recorded which are missing from the measurement values of the transmission images, preferably with the same rotation position, are calculated, preferably by resampling methods and/or interpolation methods and/or extrapolation methods.

Thus the representation and evaluation occur in a common raster in space, taking into consideration the positions of the measurement object, radiation source, and/or detector, whereby in particular, the determination of the common raster in space occurs using the volumetric data that would be produced from measurement at the highest magnification.

The possibility is offered of the measurement values, preferably grey values for the common raster, being determined from the original measurement data by means of merging and/or resampling methods, preferably when using interpolation methods, whereby in overlapping areas, preferably a weighted averaging of the measurement values occurs, in which preferably the weighting occurs as a function of the distance to the overlapping boundaries.

Preferentially, a measurement area is produced through the various relative positions between the measurement object, radiation source, and/or detector, which is larger than the measurement area covered by a fixed detector, wherein preferably a relative motion between the measurement object and at least the detector occurs in at least one direction that is nearly perpendicular to the imaging axis.

An arrangement for determining structures and/or geometry of an object by means of a measurement system, preferably a computed-tomography measurement system, consisting of at least one radiation source, at least one radiation detector, and at least one axis of rotation, is distinguished by the fact that the workpiece is rotatable about an axis of rotation different from the physical axis of rotation, with the aid of a combination of relative rotational and translational motions between the workpiece and the detector.

Thus the physical axis of rotation can be moved in at least one translational direction and/or the measurement object can be arranged to be movable in at least one translational direction at the physical axis of rotation and/or the detector can be moved on at least one translational and/or rotational axis.

There also exists the possibility that the physical axis of rotation is movable in two translational directions, whereby the first direction runs nearly perpendicular to the plane of the detector and the second direction runs nearly perpendicular to the direction of the physical axis of rotation and nearly perpendicular to the normal to the plane of the detector.

The invention further provides that the physical axis of rotation is movable nearly perpendicular to the plane of the detector and the detector is movable in at least one direction running in the plane of the detector, which runs nearly perpendicular to the direction of the physical axis of rotation, and preferably the detector is rotatable about an axis that runs nearly parallel to the axis of rotation.

Further individual characteristics, advantages, and features of the invention result not only from the claims, whose features are to be inferred, individually and/or in combination, but also from the following description of one of the drawings for the embodiment example to be inferred.

Figure 2:
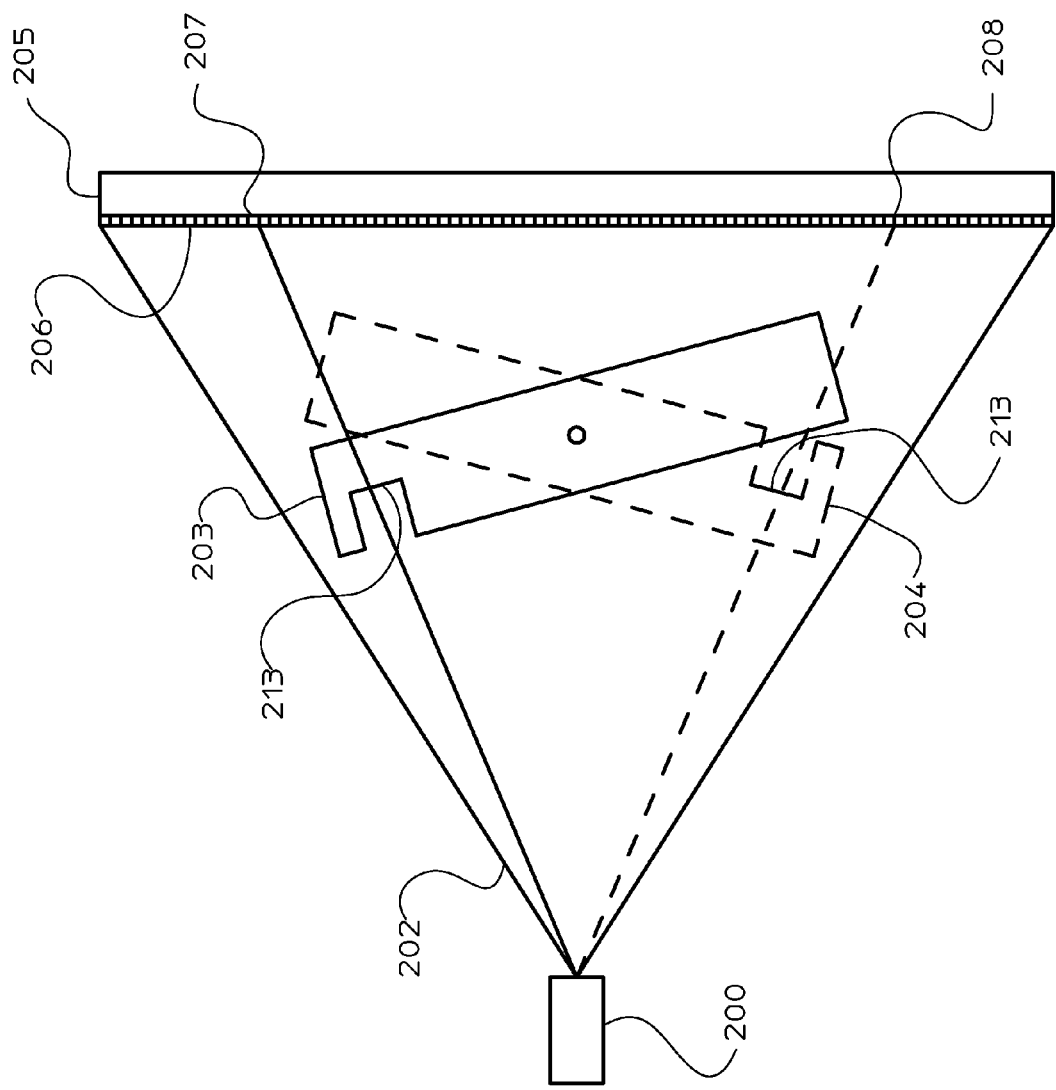
Figure 3:
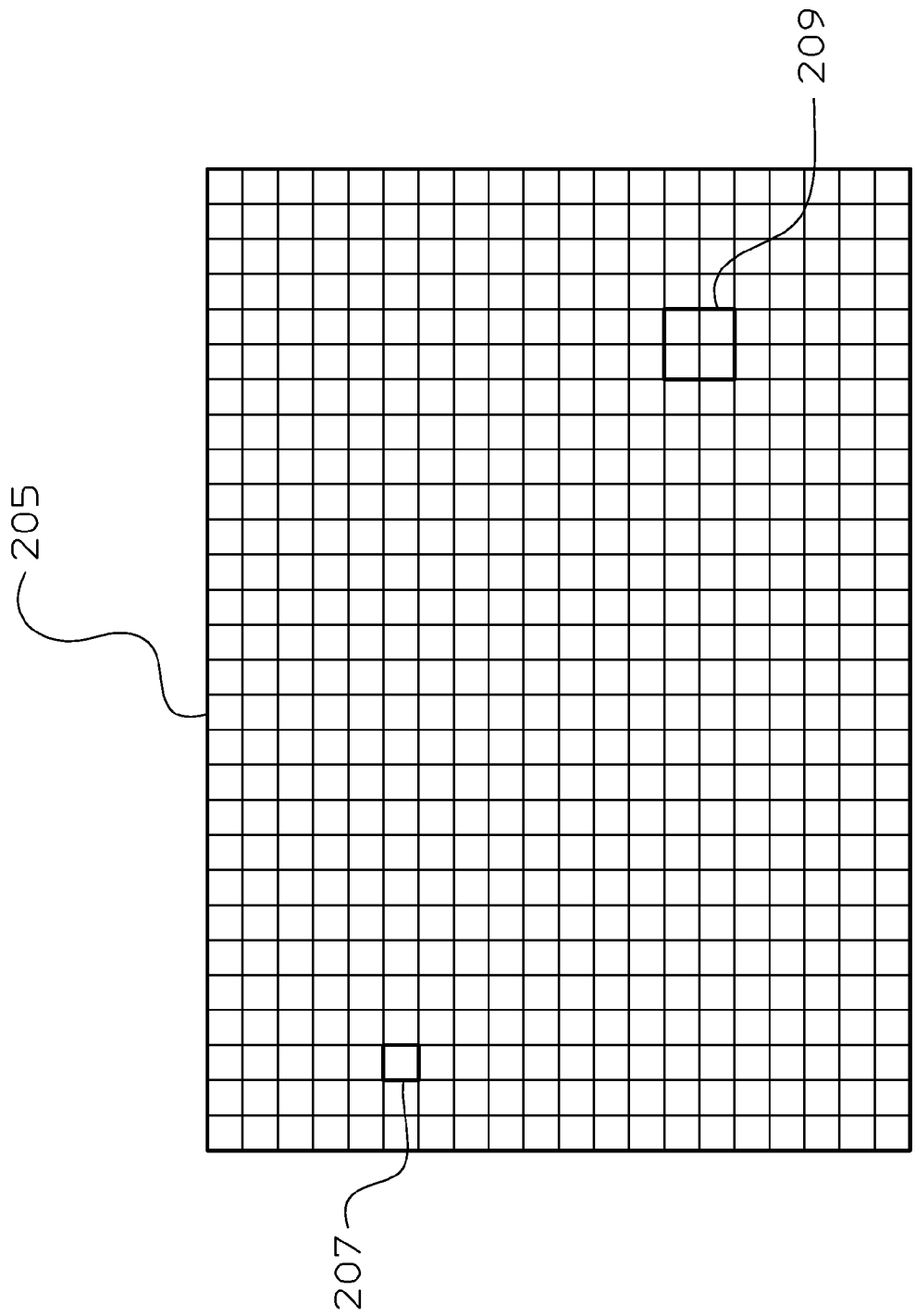
Figure 4:
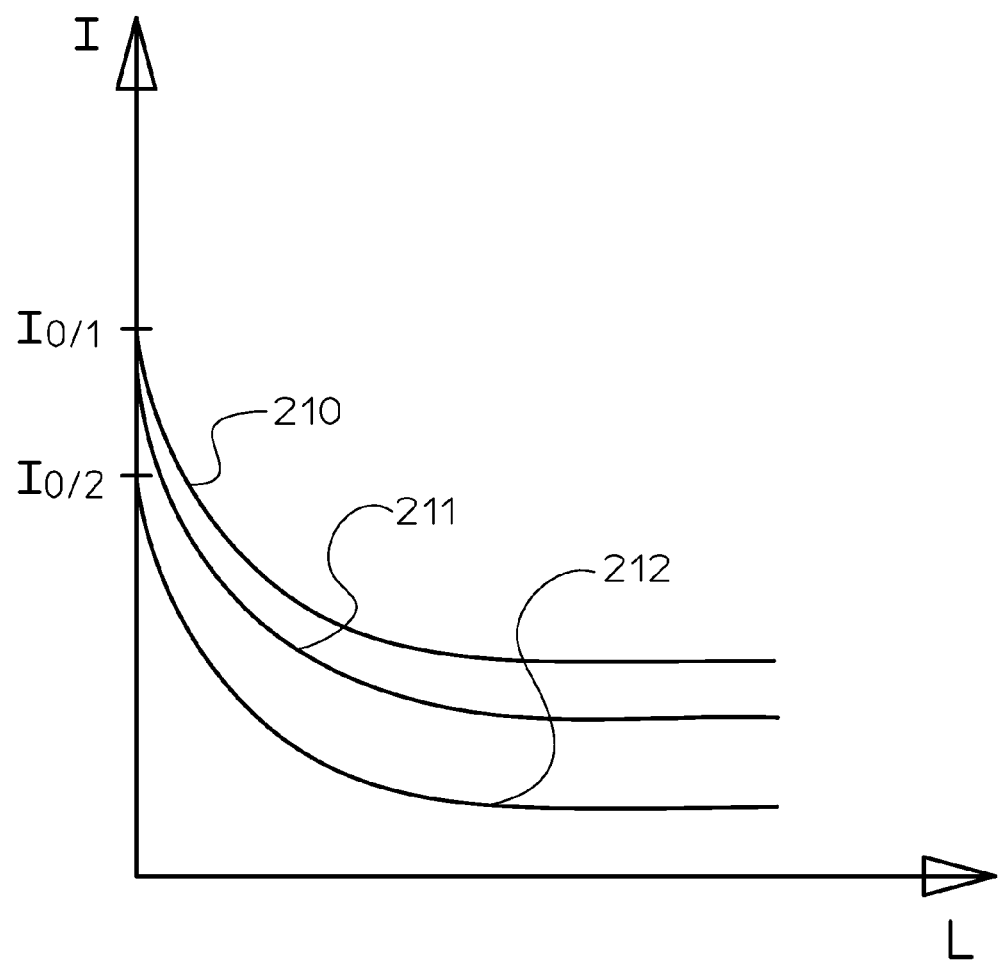
Figure 5:
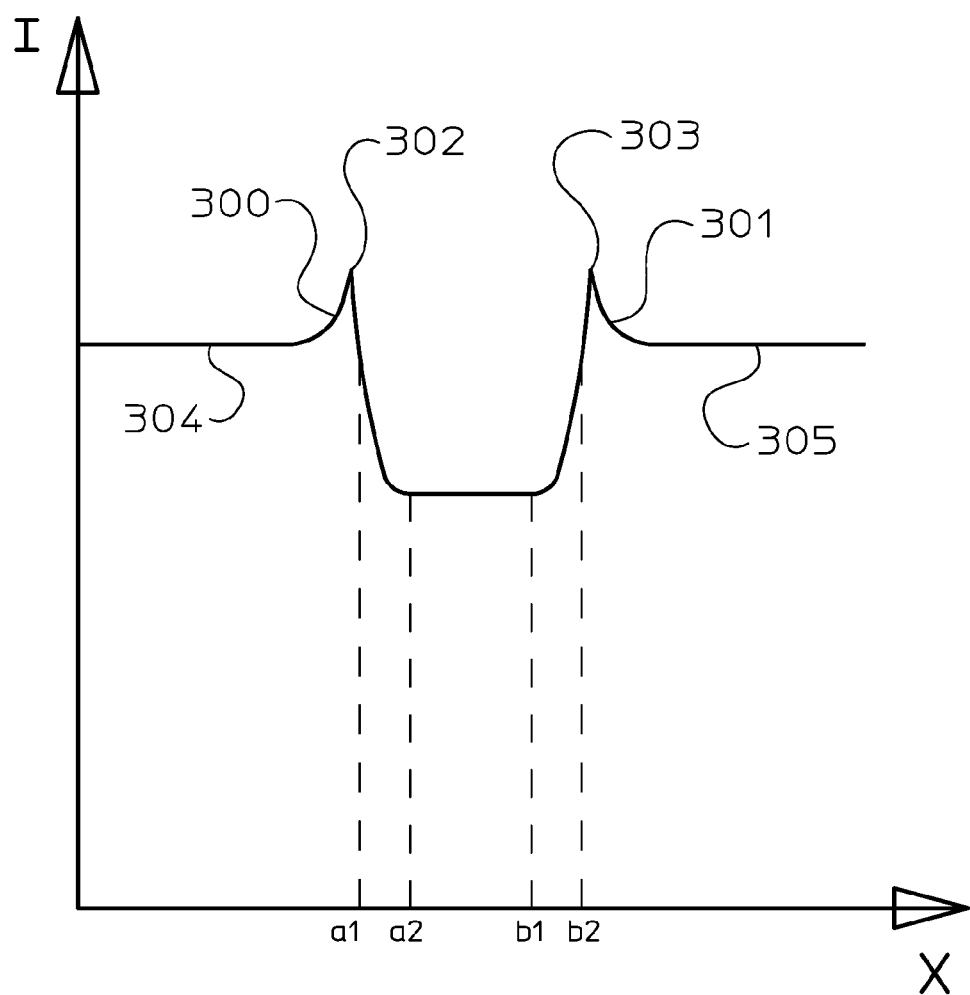
Figure 6:
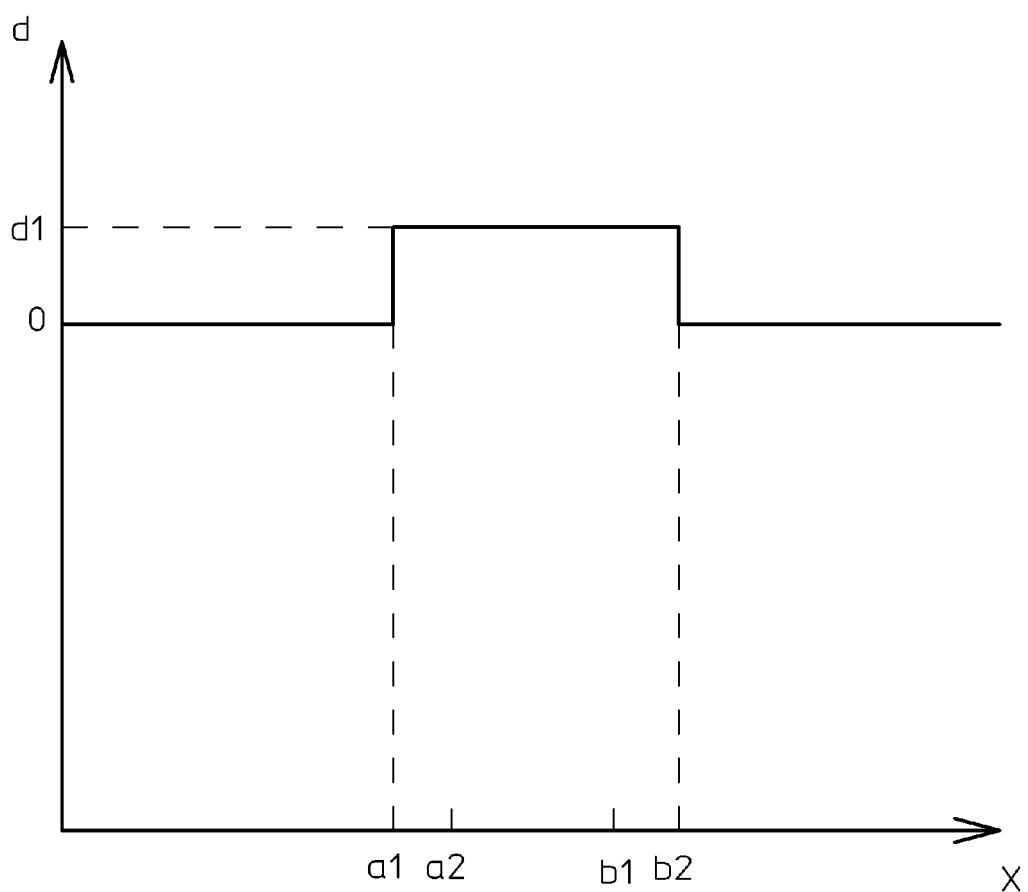
Figure 7:
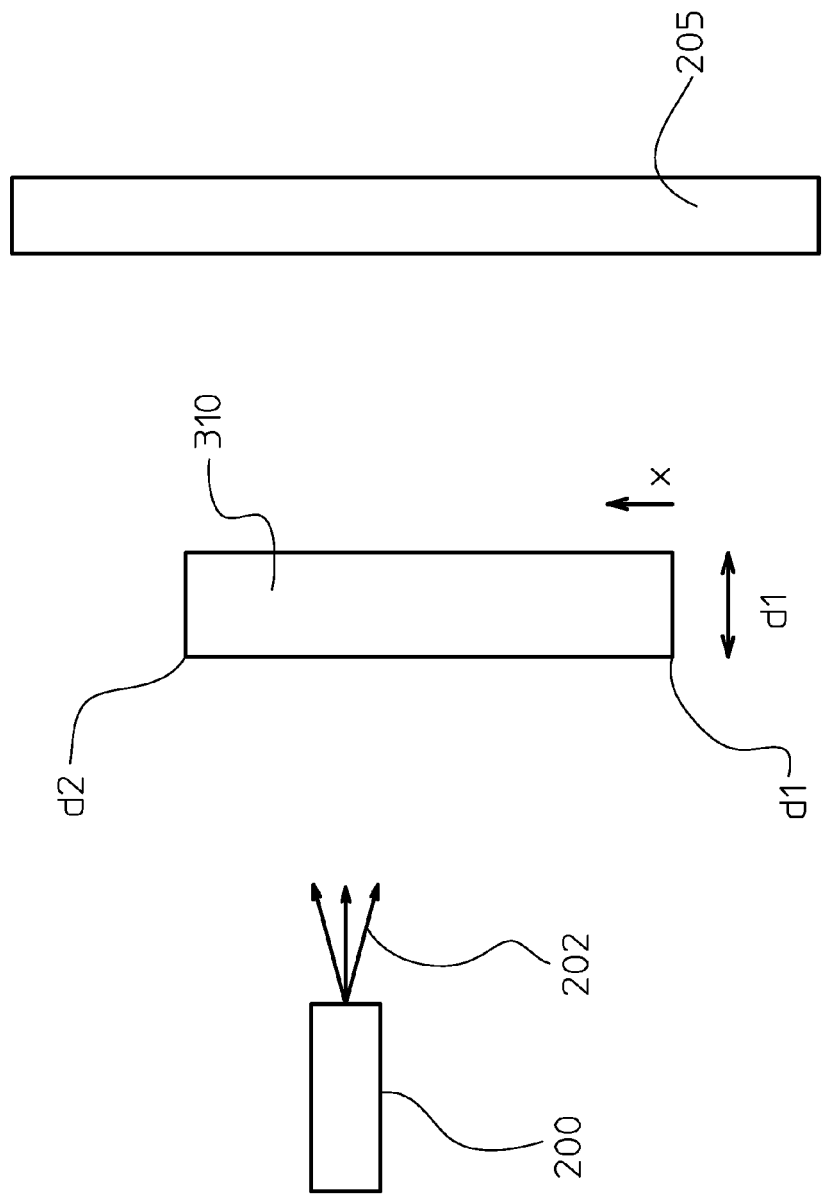
Figure 8:
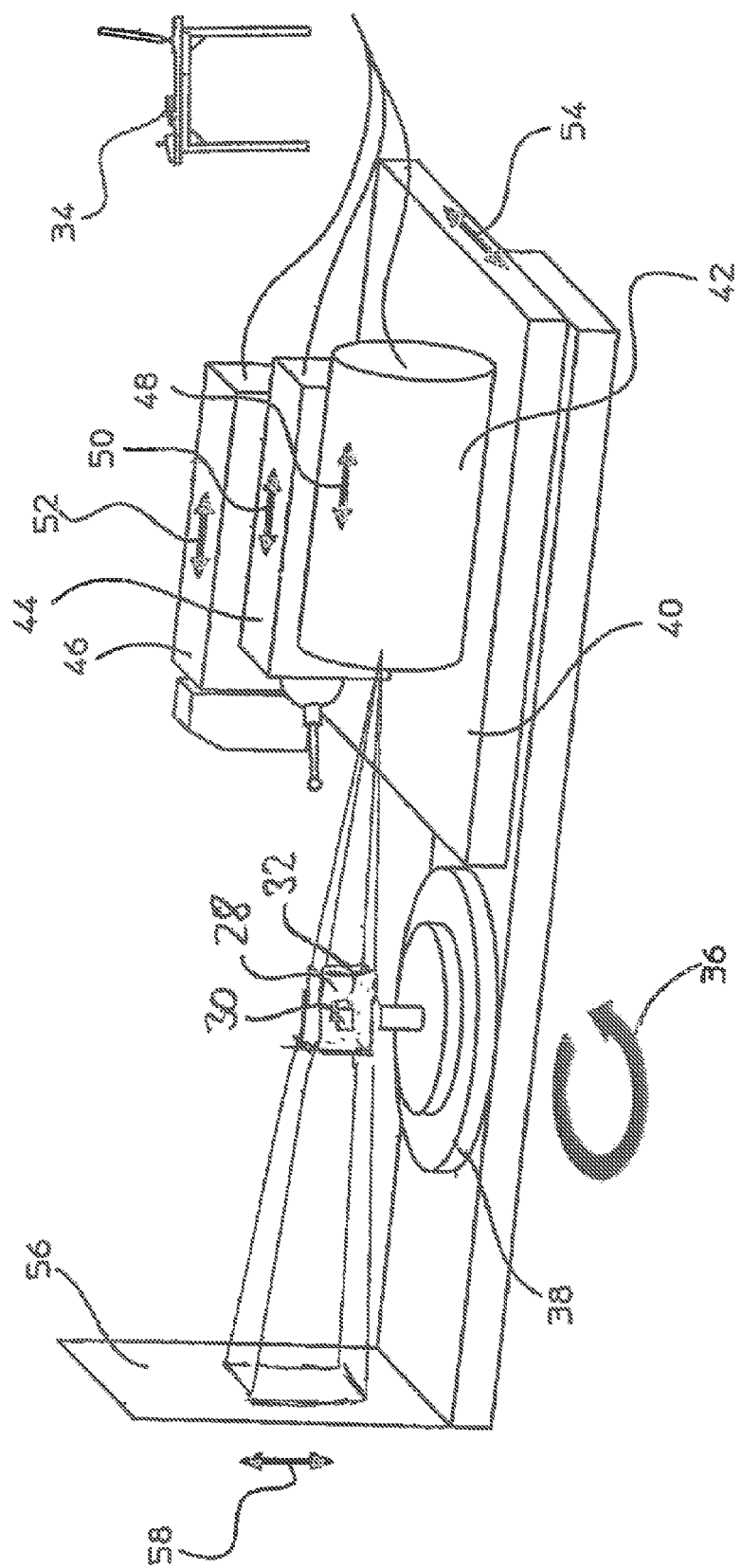
Figure 9:
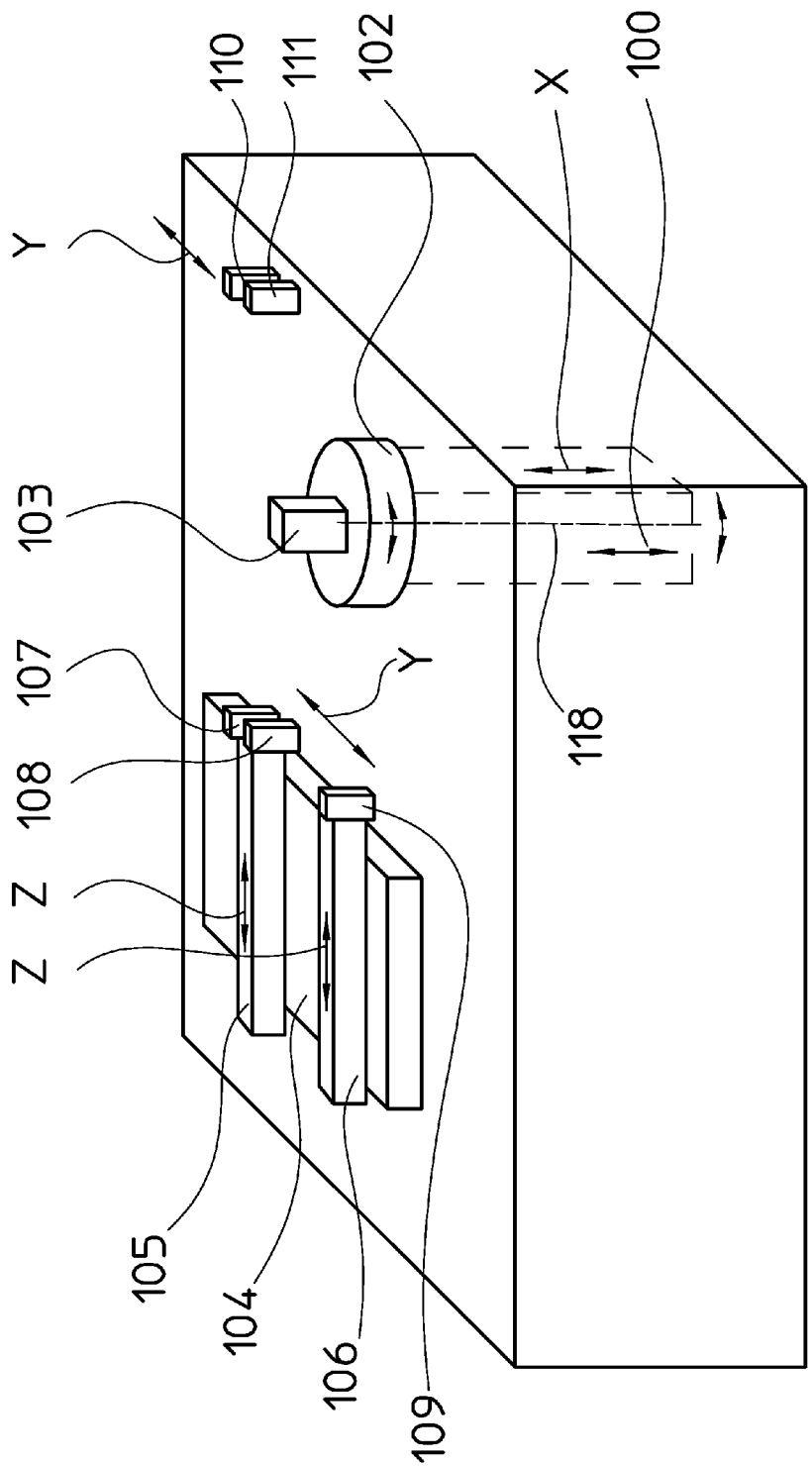
Figure 10:
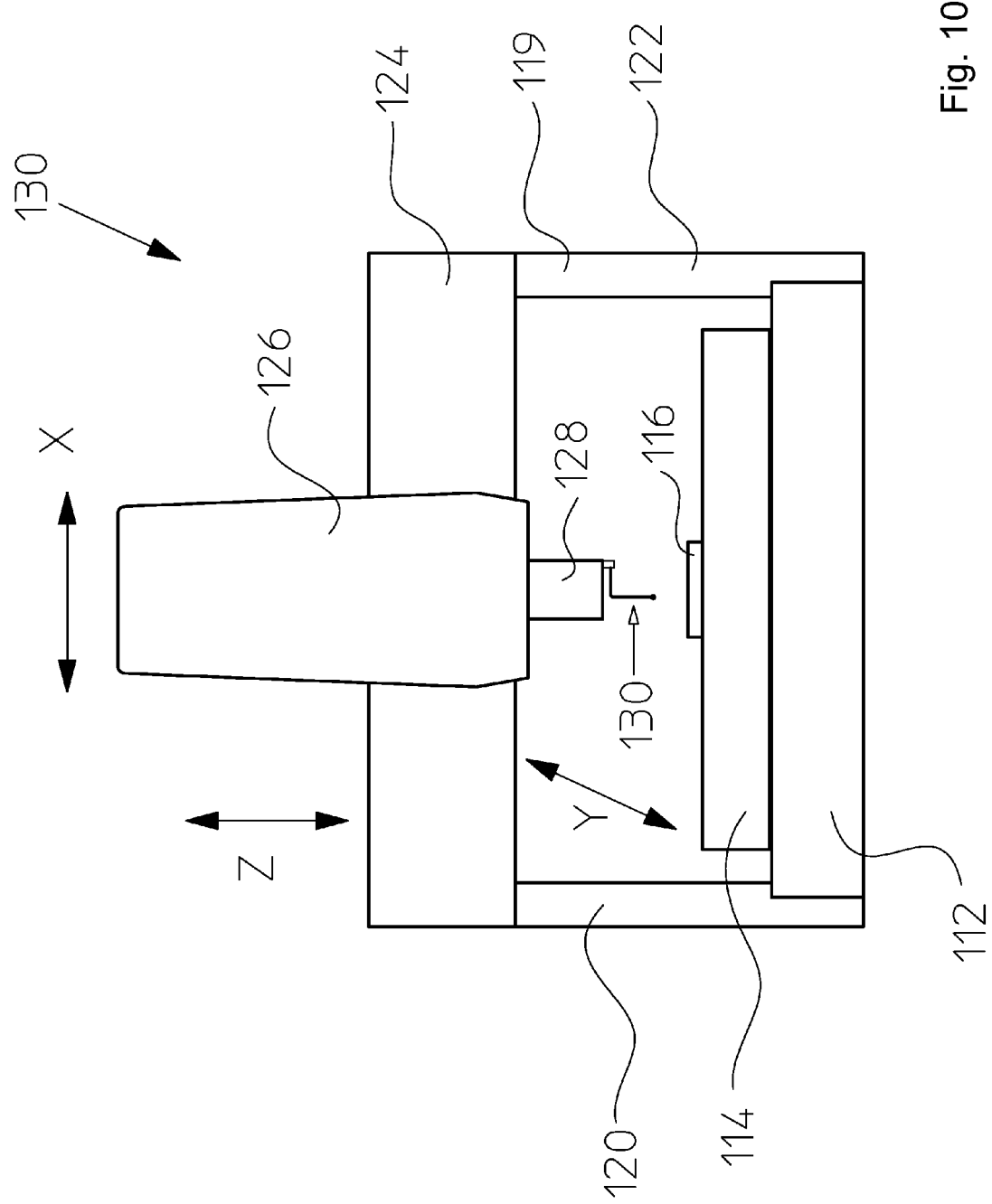
Figure 11:
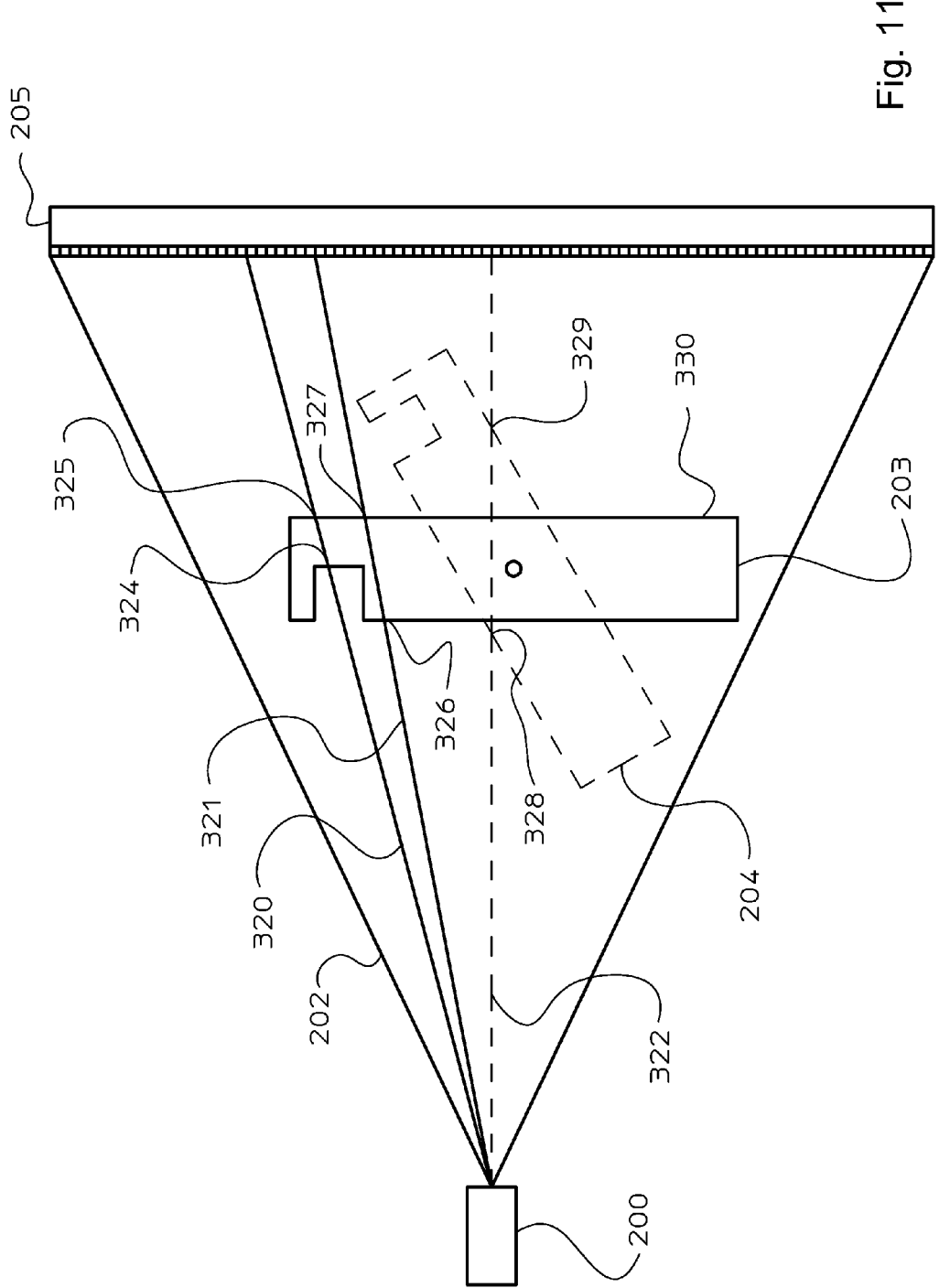
Figure 12:
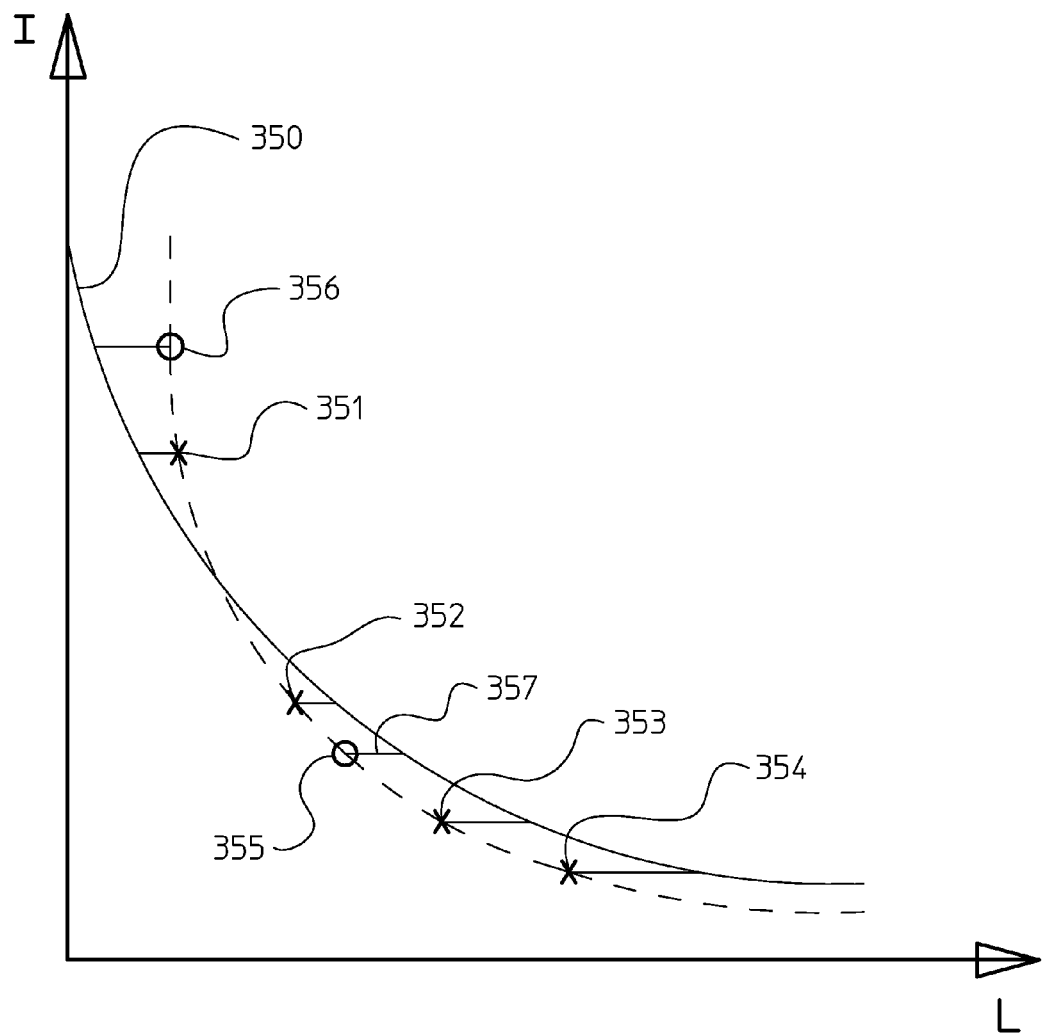
Figure 13:
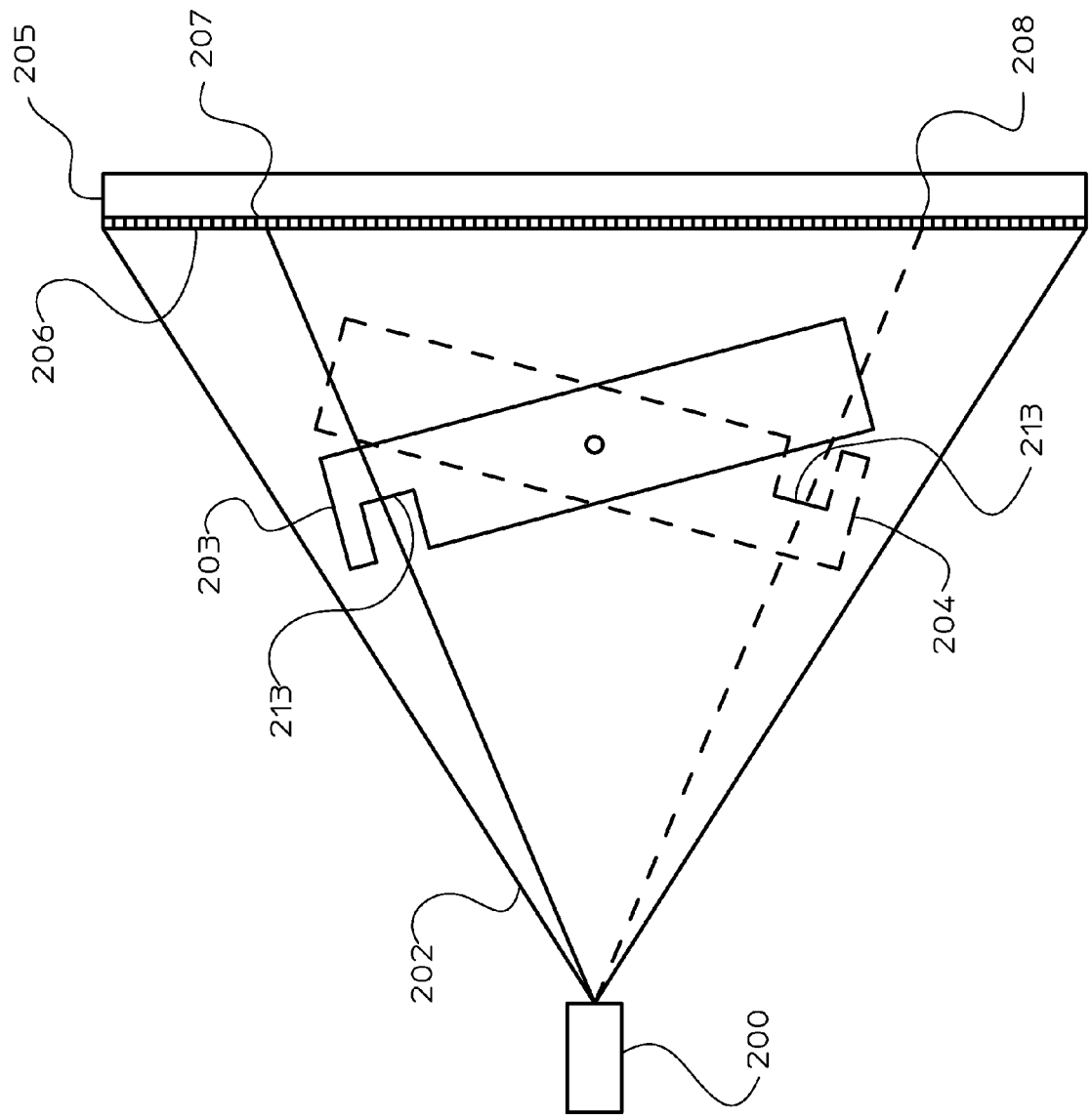
Figure 14:
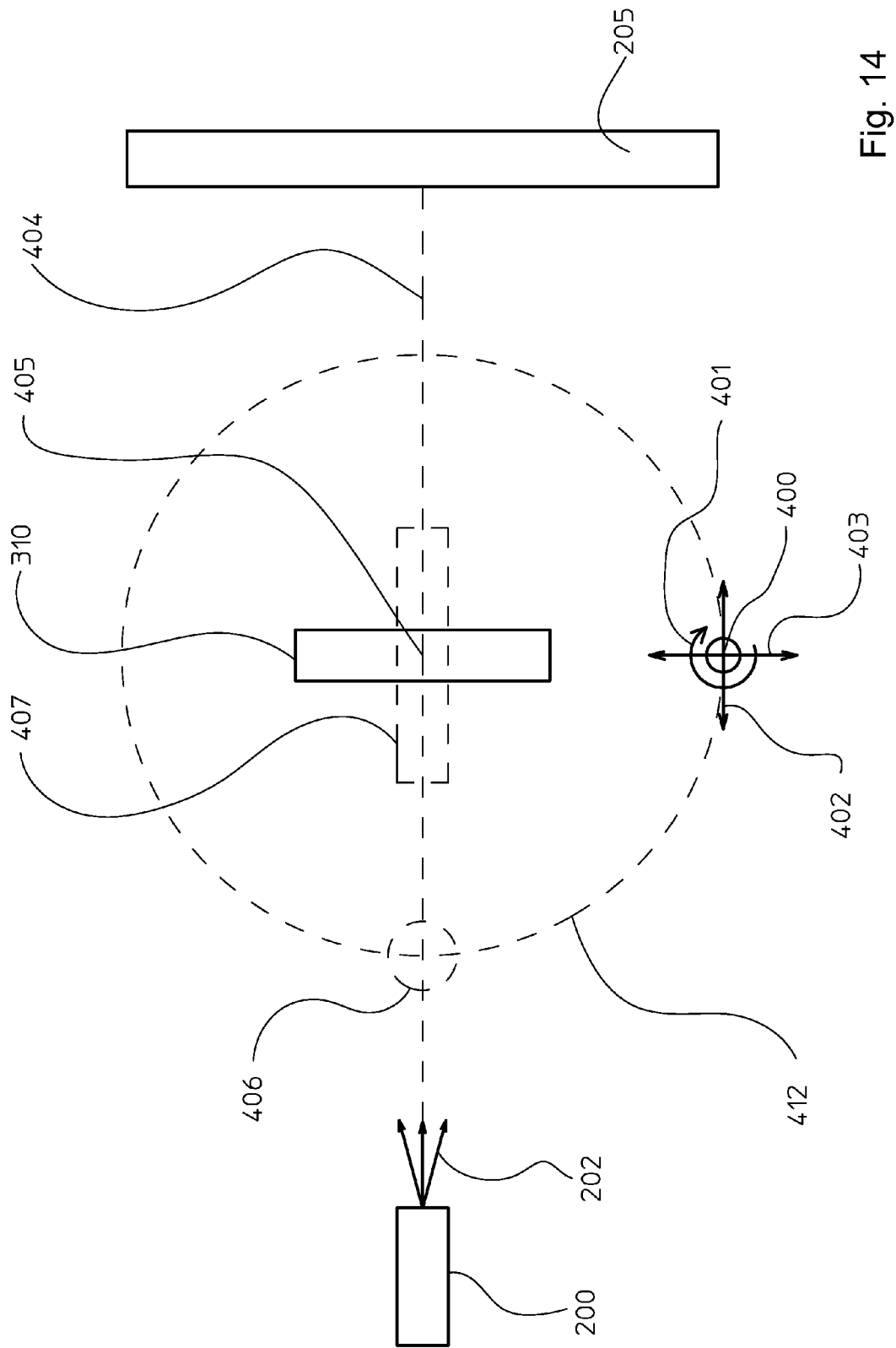
Figure 15:
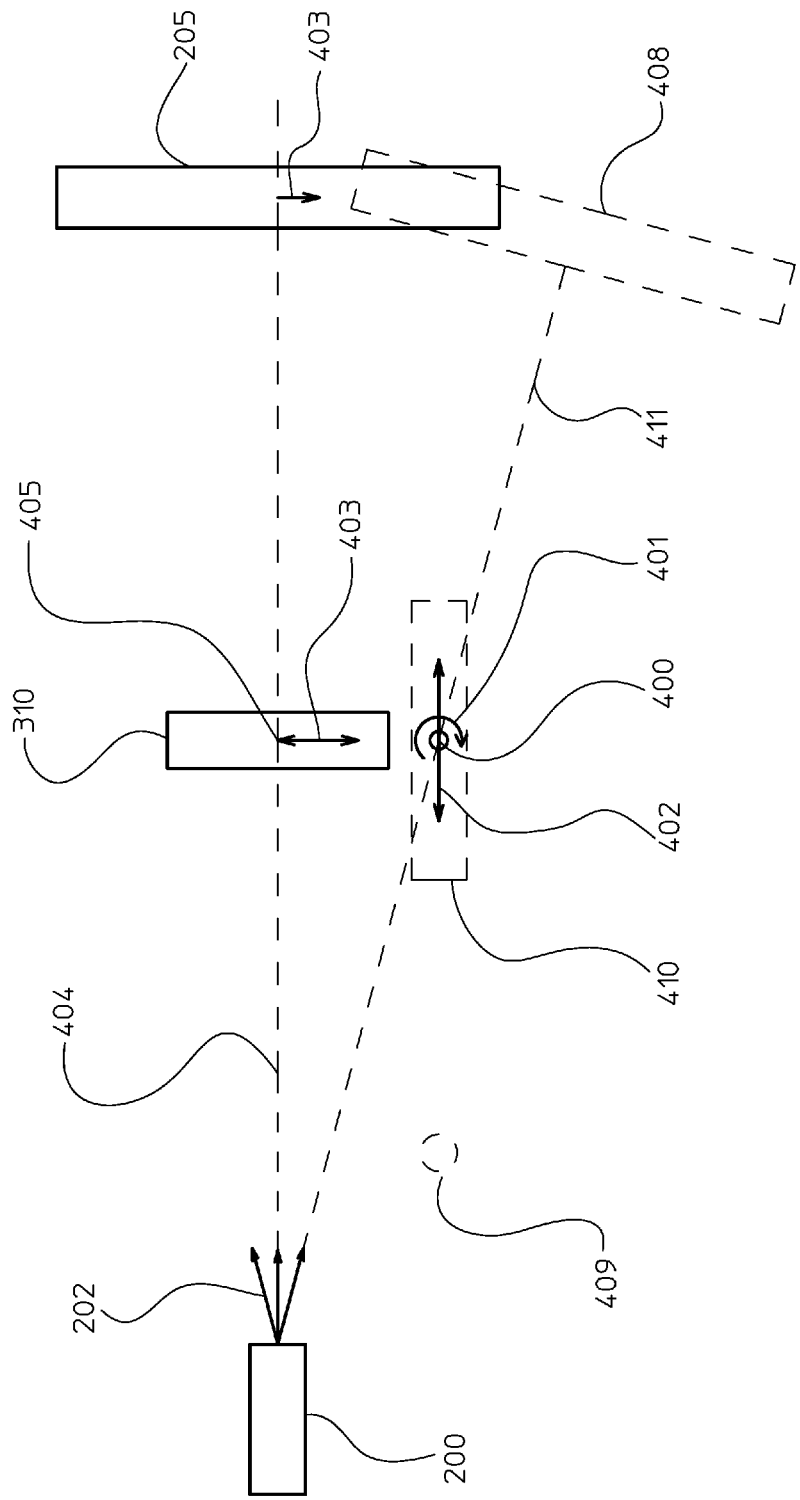
Figure 16:
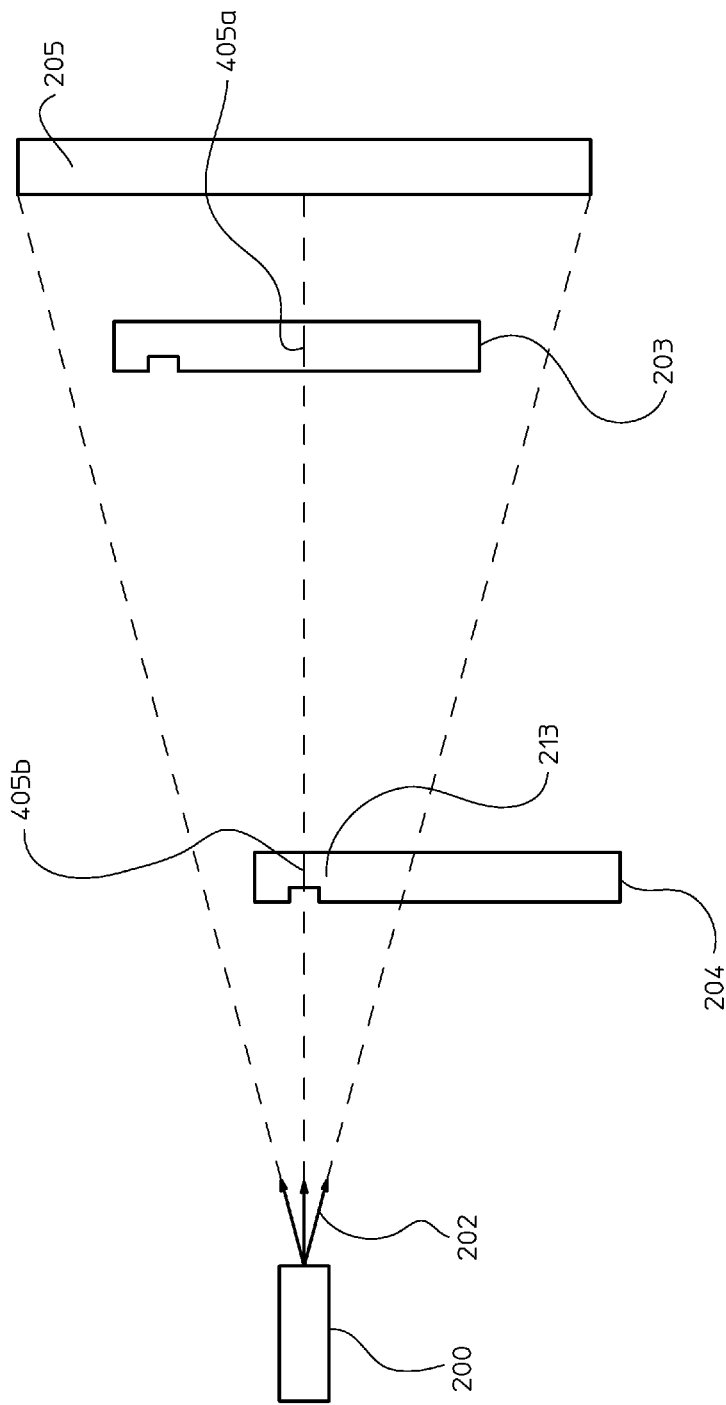
Figure 17:
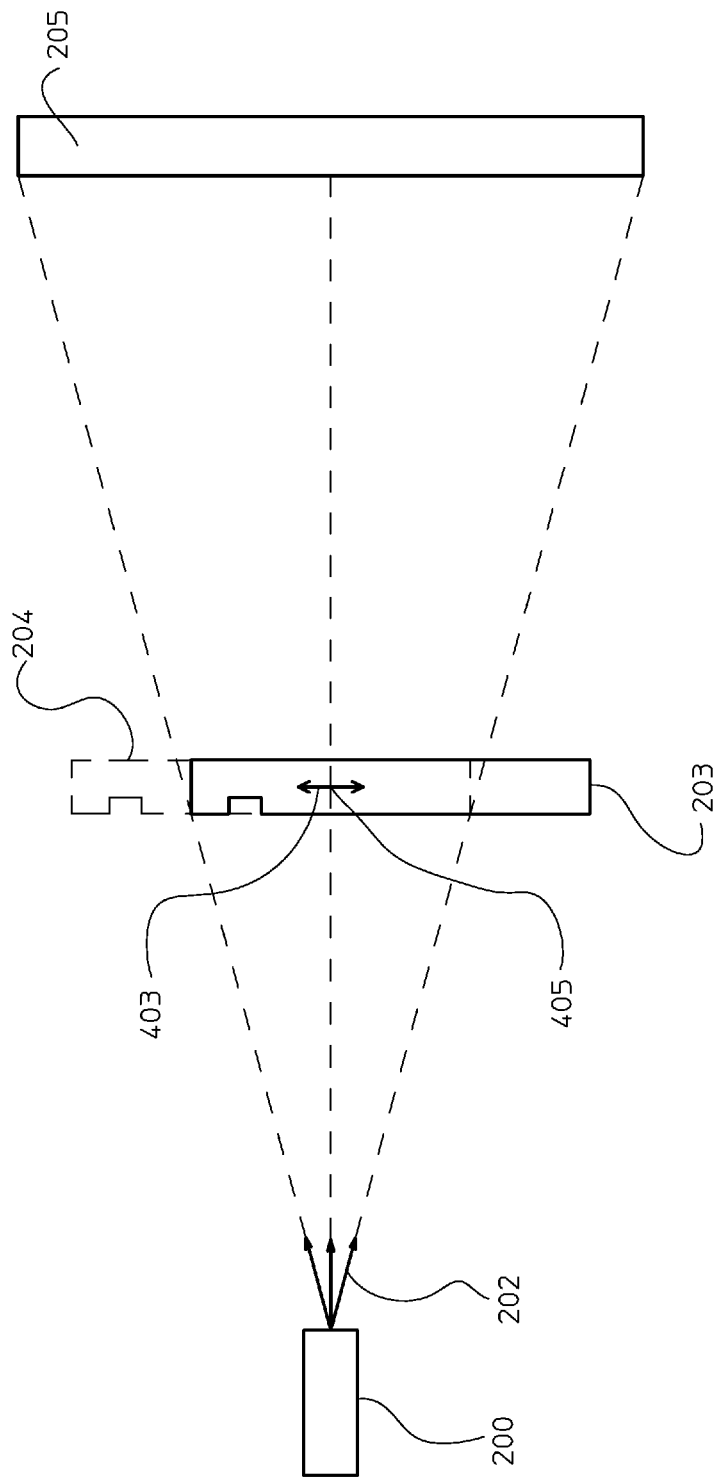

They show:

FIG. 1 a CT measurement arrangement in a principal representation,

FIG. 2 a measurement arrangement with a workpiece in two different positions, FIG. 3 a principal representation of the CT detector according to FIG. 2, FIG. 4 characteristic lines of pixels or groups of pixels in a principal representation, FIG. 5 the intensity path of measured radiation as a function of of the sites passing through a workpiece, FIG. 6 site coordinates of a workpiece corresponding to FIG. 5, FIG. 7 a principal representation of a CT measurement arrangement with the workpiece according to FIG. 6, FIG. 8 a further principal representation of a CT measurement arrangement with a workpiece, in particular for taking into consideration wobbling motions when rotating the measurement object and shifting the focus of the X-ray tube, FIG. 9 A further embodiment of a coordinate-measuring device, FIG. 10 a further embodiment of a coordinate-measuring device, FIG. 11 a computed-tomography sensor in a principal representation, FIG. 12 a principal path of an intensity distribution as a function of the transmitted length at the support point, FIG. 13 a measurement arrangement with a workpiece in two different positions FIG. 14 a first embodiment of an arrangement of an object rotatable about a virtual axis of rotation, FIG. 15 a second embodiment of an arrangement of an object rotatable about a virtual axis of rotation, FIG. 16 a first arrangement of the workpiece for the measurement of which in its entirety or of a detail of it, and FIG. 17 an arrangement for full measurement of a workpiece in two measurement to be recorded one after the other at the same magnification.

In FIG. 1, a CT measurement arrangement is represented purely as an example and in principle, which would be part of a coordinate-measuring device for measuring a workpiece 4. The arrangement includes an X-ray source 1 and an X-ray detector 5 exhibiting pixels, between which is disposed the workpiece or component 4 to be measured. The X-radiation 2 leaving the X-ray source 1 thus passes through the component 4 in different ways, whereby at the boundary surfaces of the component 4, as well as inside the component 4, radiation scatter or other artifacts can exist, which appear differently depending on the geometry of the transmission length present in the radiation direction.

In order to correct artifacts effectively appearing during the CT measurement, it is now provided that different characteristic lines of the X-ray detector 5 are used as well, for the correction of measurement values of individual pixels or groups of pixels for the CT detector used. At the same time, the different measurement-engineering properties of the individual pixel or groups of pixels and/or artifacts are determined in computed-tomography imaging to determine individual characteristic lines. The effects due to artifacts are considered in the characteristic lines, wherein the transmission lengths assigned to the individuals pixels or groups of pixels and/or the geometry of the workpiece 4 at the various rotation positions are determined to record various projection data during CT measurement.

Determining the transmission lengths and/or the geometry of the workpiece 4 at the various rotation positions can occur using the current, nearly complete projection data or using a CAD model.

To correct for artifacts from pre-determined transmission lengths and/or the characteristic geometry present in the respective transmission direction, one or several parameters are derived, which are then taken into consideration in the characteristic lines.

In particular, the parameters are derived from the characteristic geometry, wherein the line segments transmitted from the geometry and/or material sequence are determined for each type of material and arrangement and the formation of artifacts such as radiation scatter and beam hardening is inferred therefrom.

Alternatively, the parameters can be derived from the characteristic geometry, wherein a weighted average transmission length of an individual material sequence or an otherwise analytically formed contrast ratio is determined from the geometry and/or material sequence, for example with the aid of simulation and also therefrom the formation of artifacts such as radiation scatter and beam hardening is inferred. What is more, different characteristic correction lines will also be determined and used, depending on the rotation position and/or position of the workpiece as well as of component 4.

The selection and assignment of the respective characteristic lines for the individual detector pixel and/or groups of pixels of the X-ray detector 5 occurs at the respective rotation position and the position of the workpiece 4 by means of alignment with the workpiece.

In FIG. 2, a workpiece 203 is represented, purely in principle, which is penetrated by X-radiation 202 emitted from a CT tube (X-ray source) 200, whereby the X-rays 202 appear at a detector 205. In a first position of the workpiece 203, X-rays which penetrate an area 213 of the workpiece 203 are detected by the detector pixel (X, Y) 207, while in a second divergent position of the workpiece 204, it penetrates the same area 213 but is detected by the pixel (X+N, Y+M) 208. The detector pixel (X, Y) 207 detects X-radiation which has penetrated another area 203, 204 of the workpiece, which differs particularly in the transmitted length and/or the material sequence transmitted. Artifacts which depend on the length transmitted and/or the material sequence, such as, in particular, beam-hardening or radiation-scatter artifacts, are thus expressed differently at the various rotation positions of the workpiece. In order to take this dependence into consideration, it is provided according to the invention, among other things, that different characteristic lines are also determined and considered for the different pixels or groups of pixels, at different rotation positions of positions of the workpiece, which describe the relationship between the component length and/or material sequence transmitted and the radiation intensity detected.

Thus, FIG. 3 shows the CT detector 205 and an individual pixel 207 or a group of pixels 209. Different characteristic lines according to the invention are used for the individual pixel 207 or group of pixels 208, which describe the relationship between the component length L transmitted or of the material sequence and the beam intensity I detected.

By way of example, three different characteristic lines 210, 211, and 212 are represented in FIG. 4. These can be differentiated on the basis of the physical properties of the individual pixels or groups of pixels and/or the transmitted path length of the workpiece or the material sequences within the workpiece, for example, at the initial intensity $I_{0/1}$ or $I_{0/2}$, as well as in their gradient behavior or linearity.

Using FIGS. 5 through 7, it will be clarified by way of example how the intensity of radiation scatter is determined in order to then use this for correction.

In FIG. 5, the path of the intensity I is expressed by way of example as a function of the site X for a cross-section through a single transmission image of a workpiece 310, which is represented in more detail in FIGS. 6 and 7. The workpiece 310 is arranged according to FIG. 7 between the X-ray source 200 and the detector 205 corresponding to the drawn representation and is penetrated by radiation 202 from the X-ray source 200. Between the sites a1 and b2, the workpiece 310 exhibits a density d1 in the transmission direction. In FIG. 6, the density of the workpiece 310 is once again represented as a function of the site X. Corresponding to the representation in FIGS. 5 and 6, the corners of the workpieces 330 are in the area between the sites a1 and a2 or the sites b1 and b2. Between the two corner sites a clearly lower intensity is available than in the areas 304 and 305 far outside the workpieces 310. Outside the workpiece 310, but close to the corner sites, are the areas 300 and 301 with higher intensity, which can be triggered by radiation scatter, for example. The maxima 302 and 303 can be used to determine the intensity of radiation scatter compared with the intensity of the unattenuated X-ray from areas 304 and 305. Detector pixels that are disposed between the sites a1 and b2 can be corrected, reduced, for example, around the amplitude of radiation scatter. The corrections can moreover be used for all pixels uniformly or as a function of the current transmission length or the line segments transmitted for each type of material.

A multisensor coordinate-measuring device for taking wobbling motions into account during the rotation of the measurement object or shifts between the X-ray tube, particularly the focus of the X-ray tube, and the X-ray detector may be inferred purely in principle from FIG. 8, with which a full dimensional measurement of a workpiece 28 can be made, which, for instance, consists of a core 30 and a shell 32 enclosing it. The materials of the core 30 and shell 32 diverge in their densities. Thus the core 30 is made of metal and the shell 32 of plastic or another lighter substance.

The coordinate-measuring device is connected to an evaluation unit 34 with controls, hardware, and software, as well as to a storage unit for storing the measurement points. Furthermore, an input and output unit is available for an operator.

The workpiece 28 is arranged on a rotatable table 38. An X-ray source 42 and, for example, both a tactile sensor 44 and a laser-line sensor 46, are disposed on a carrier, which are movably arranged along travel axes on the carrier 40 (double-arrows 48, 50, 52). The carrier itself is movable along an axis 54 running perpendicular to the travel axes 48, 50, 52.

On the side of the workpiece 28 facing the X-ray source 42 is arranged an X-ray detector 56. It can moreover be moved, depending on the measurement task of the detector 56 perpendicular to the travel axes 48, 50, 52, 54 and, if necessary, parallel to the travel axis 54 of the carrier 40.

In this embodiment example, the workpiece 28 is penetrated by the X-radiation emitted by the X-ray source 32. The radiation penetrating the workpiece 28 is then determined by the detector 56. In order to unambiguously assign the transmission images spatially to one another which serve for reconstruction at the various rotation positions of the workpiece 28 and measurement accuracies thus exclude or minimize in the perimeter any sort of wobbling motion while rotating the workpiece 28 or shifts between the X-ray source or X-ray tube 42, particularly its focus, and the X-ray detector 56, so that the desired measurement accuracy is ensured, pre-information is taken into consideration, by means of which the transmission images are corrected in the measurement process itself. For this, one or several pre-transmission images of the workpiece 28 or parts of it are recorded first. In order to minimize drift phenomena in the pre-recording, only a few little transmission images are recorded at a few different positions. By comparing the pre-recorded transmission images or parts thereof and the transmission images or parts thereof recorded during the measurement, a shift or scaling can be recognized and corrected, with the aid, for example, of correlation methods. This can occur, for example, by means of resampling methods or positioning the X-ray source 42 relative to the X-ray detector 56 and/or the workpiece 28.

If transmission images for which no pre-transmission images exist are used for measurement, they are corrected with the aid of interpolation methods from pre-recorded transmission images for adjacent rotation positions of the workpiece 28. In particular, it is provided that 20 to 70 pre-transmission images are recorded compared with the 100 to 1600 transmission images that are typically required for measuring the workpiece 28.

In FIG. 9, a coordinate-measuring device is represented purely in principle for the combined use, if necessary, of an X-ray sensor system and an optical and/or tactile sensor system.

A rotating table 110 is arranged on an axis 118 running parallel to the X-axis of the coordinate-measuring device. On this is a measurement object 103 and thus it can be rotated about a rotation axis 118 and moved in the X direction through the axis 118 (double-arrow). Two axes 105, 106 are arranged running parallel to the Z-axis on a bolt 104 running parallel to the Y-axis. On the mechanical axis 105 are a sensor 107 for X-radiation and an image-processing sensor 108. In addition a tactile sensor 109 is on the mechanical axis 106. An X-ray source 110 is disposed opposite the X-ray sensor 107, which can be introduced as movable or fixed, as desired, in the Y direction. Opposite the image-processing sensor system 108 is a transmitted light source 111. The mechanical axes and bolt, which run along the X, Y, and Z axes of the coordinate-measuring device, are laid out such that the sensors installed on or at the coordinate-measuring device can respectively cover the whole measurement area at the rotating table 102.

By integrating computer tomography (CT) into a multisensor coordinate-measuring device, new possibilities are totally created. Rapid, complete, failure-free measurement with tomography with high-precision functional measurements is combined with a tactile or optical sensor system. At the same time, it can be provided that the X-ray sensor system (sensor, radiation source) can be positioned corresponding to a second sensor system (for example, an image-processing sensor, transmitted or direct-light radiation source, or tactile sensor, if necessary, with assigned image-processing sensor) in the coordinate-measuring device, so that the X-ray sensor system is identically arranged as well for a second sensor system. At the same time, the X-ray sensor system can be arranged with at least the tactile sensor system and/or the optical sensor system on a common mechanical axis or on a separate mechanical axis, which operates in a manner analogous to the mechanical axes for the tactile and/or optical sensor system. The layout of FIG. 9 for the coordinate-measuring device being inferred as a multisensor coordinate-measuring device is not required for the complication of all parts of the teaching according to the invention. Rather, it is only guaranteed that computed tomography can be performed.

In FIG. 10, a further embodiment is represented, purely in principle, of a multisensor coordinate-measuring device 130. The sensors can be assembled or disassembled as desired or can also be interchanged or replaced automatically by suitable sensor replacement systems during operation. Of course, the invention does not rely on whether a corresponding number of selected sensors is calmly mounted on the device in order to measure objects in this configuration.

The sufficiently well-known principle depicted once more in FIG. 10 of a coordinate-measuring device 130 includes a base frame 112 made of granite with a measuring table 114, on which a object 116 to be measured is positioned in order to measure its surface properties.

Along the base frame 112 a portal 119 is movable in the Y direction. For this, columns or stands 120, 122 flexibly support the base frame 112. From the columns 120, 122 a crossbeam 124 extends, along which a carriage can travel, which for its part admits a spindle sleeve or column 126, which is movable in the Z direction. From the spindle sleeve 126 or, if necessary, a replacement section 128 connected to the spindle sleeve 126 extends a sensor 130, which can be constructed as a tactile sensor, which, when the spindle sleeve 126 contains an image-processing sensor, measured tactilely and optically. However, so far as the sufficiently well-known prior art is concerned, in the same way as in reference to further sensors being realized for use such as a laser-distance sensor, a white-light interferometer, image-processing sensors, an X-ray sensor system, or a chromatic focus sensor or confocal scanning measurement head, without any limitation occurring because of this in the teaching according to the invention. The sensor or sensors are selected and used according to the measurement task, in order to optimally configure the coordinate-measuring device 130 for the respective measurement task. At the same time, problem are solved which appear in the usual coordinate-measuring devices.

In order to be able to use the coordinate-measuring device 130 with a suitable sensor, the coordinate-measuring device can exhibit a sensor exchanger. Thus several sensors can be provided respectively as desired on a replacement section with the coordinate-measuring device 130 and can be replaced by hand or by automatic pickup from a parking station.

FIG. 11 shows a principal representation of a computed-tomography sensor. The radiation 202 leaving the X-ray source 200 penetrates a workpiece 203 and thereafter strikes a detector 205. In order to produce the relationship according to the invention between the attenuations values determined by the detector 205 and the corresponding transmitted lengths of the workpiece or component 203, the points of intersection 324, 325 for the ray 320, for example, with an optical or tactile sensor are measured. Further support values can be determined for the characteristic correction line, as well as other transmission lengths, for example by using a ray 321 and measurement from the points of intersection 326, 327 or also by using a ray 322 from the points of intersection 328, 329 through the measurement object with changed rotation position 204.

An alternative possibility for determining the transmission length between points of intersection, e.g. 326 and 327, consists of determining the coordinates of the points of intersection by means of the mathematical combination of tactilely and/or optically measured elements, for example planes or cylinders, and/or hand elements. For instance, the coordinates of the intersection point 327 through the edges of a tactilely and/or optically measured plane 330 are determined with a hand line, which runs along the ray 321.

The lengths appearing between these transmission lengths can be determined by means of interpolation. In this same way, it is possible to determine longer or shorter transmission lengths by extrapolation and to bring them into a functional relationship with the attenuation values of the detector.

FIG. 12 shows furthermore the relationship between the transmitted length L and the intensity I determined by the detector. Proceeding analytically from an existing characteristic line 350 existing or in the form of a look-up table (LuT), correction values are first determined for the discrete measured points 351 through 354 as a difference length for the characteristic line at hand. For intensities lying between these support points, for example the one characterized by the point 355, the correction 357 is determined by interpolating the point 355. It is likewise valid for intensities lying outside the support points, for instance the one that runs through the point 356 by using extrapolation methods. The correction values assigned to individual intensities are recorded and used in the form of analytic functions or value tables LuT.

Using FIG. 13, which is identical to FIG. 2, further essential aspects of the teaching according to the invention will be clarified for performing computed tomography. Thus, in FIG. 13 an object or workpiece 203 is represented purely in principle, which is penetrated by X-radiation 202 emitted from a CT tube 200, whereby the X-radiation 202 appears at a detector 205. In a first pre-set rotation position of the workpiece 203, the radiation being received by a detector pixel 207 of the detector 205 penetrates the measurement object 203 in an area 213 and produces a corresponding characteristic grey values at the detector pixel 207. In further representations, rotation position 204, for example, further characteristic grey values exist for the various detector pixels, for instance detector pixel 207 or 208. If at least one area from 0 to 90 degrees is covered in the various rotation positions, then the shortest and longest transmission lengths are contained at least once in the image as the detector 205. A darkest and brightest pixel and a contrast value therefrom are calculated or a histogram of pixel grey values for statistical evaluation. If the brightest pixel is more than a predetermined maximum value, and the image is partially overcontrolled for example, then parameters such as the current of the CT tube 200 and/or the integration time are automatically reduced, for instance, in order to then take pre-transmission images again in advance.

With the appearance of pixels below a pre-determined limiting values, the parameters, for instance the number of image averagings, is automatically increased, whereby the signal transport distance is increased, as well as improved, in order to then take pre-transmission images again.

For instance, if a very large number of very dark pixels are in the image area evaluated, then an increase in the beam voltage of the CT tube 200 occurs automatically and thereafter pre-images are recorded again. The opposite approach is taken for a very high number of very bright pixels.

FIG. 14 shows an X-ray source 200 and one of its outgoing measurement rays 202, an X-ray detector 205, and a workpiece 310 disposed between these in a first measurement position, which is connected firmly to the physical rotation axis 400. The first measurement position is assumed, wherein by moving the physical axis of rotation 400 in the direction of the arrow 403 (running vertically in the drawing), the virtual axis of rotation 405, which corresponds approximately to the axis of symmetry of the workpiece 310, is aligned approximately with the detector 205, as well as being cut approximately by the central ray axis 404. By rotating the physical axis of rotation 400 (in the drawing, about one of the axes cutting the plane of the drawing perpendicularly) in the direction of the arrow 401, transmission images of the workpiece 310 are recorded in several, typically 100-1600, steps up to 360°. Thus, at all the rotation positions, the workpiece is completely imaged at the detector, at the same time the axis of rotation 400 bearing the workpiece 310 in the direction of the arrows 402 (running horizontally in the drawing) and 403 moves so that the virtual axis of rotation 405 assumes the same position in all rotation positions for the detector 205. For the 90° position, for instance, the position of the physical axis of rotation 406 and of the workpiece 407 is represented. The movement of the physical axis of rotation in the direction of the arrows 402 and 403 occurs by means of a mechanical stage, which is part of a coordinate-measuring device in which the arrangement is introduced on a circular path 412.

In FIG. 15, the physical axis of rotation 400 now only travels in the direction of the arrow 402, while at the same time the detector 205 moves in the direction of arrow 403 and preferably wobbles additionally about an axis parallel to the physical axis of rotation 400. In addition, the virtual axis of rotation 405 cuts the central ray axis 404. For the 90° position, for example, the changed position of the axis of rotation 409, the workpiece 410, and the detector 408 are represented. The virtual axis of rotation is now at the starting position of the physical axis of rotation 400 and once more cuts it now drifting with the detector 205e, as well as the rotated central ray axis 411. In the further path of rotation for the physical axis of rotation 400, the virtual axis of rotation 405 is moved in the direction of arrow 403.

FIG. 16 shows the workpiece 203 in a first position for determining the full geometry and in a second position 204 for high-resolution determination of a detail 213 at high magnification. In the first position, the rotation of the workpiece 203 occurs about the virtual axis of rotation 405a (in the drawing, about one axis cutting the drawing plane perpendicularly) and the workpiece is fully imaged in all rotation positions at the detector 205. In the second position, the rotation of the workpiece 204 occurs about the virtual axis of rotation 405b (in the drawing, about one axis cutting the drawing plane perpendicularly). In this position, part is missing in at least a few rotation positions of the radiation area 202 formed by the X-ray source 200 in the drawing plane or on at least one plane that is intersected perpendicularly by the virtual axis of rotation 405b. The workpiece is thereby not fully imaged in all rotation positions at the detector 205. The transmission values thus missing at the detector 205 are then determined from the measurement in the first position of the workpiece 203 by resampling methods with the aid of interpolation methods and/or extrapolation methods. The results of both computed-tomography measurements are extended into the combined connection, wherein the reconstructed grey values are recalculated on a combined three-dimensional raster with the aid, for example, of resampling methods using interpolation methods.

FIG. 17 shows the same approach as FIG. 16, whereby, however, at approximately the same magnification the partially recorded overlapping areas of the workpiece 203 are combined, which were measured in the positions 203 and 204 one after the other. Thus, the workpiece 203 can be completely determined, although it is larger than the measurement area that is formed by the detector 205. The virtual axis of rotation 405 rotates thereby either about an axis cutting the drawing plane perpendicularly or about the arrow 405 (running vertically in the drawing).

The invention claimed is:

1. A method for determining structures, geometry, or both, of a workpiece by means of a computed-tomography measurement system, the method comprising providing an X-ray source, at least one X-ray detector, and a physical axis of rotation of a rotating support on which the workpiece is stationarily arranged, wherein:
transmission images, originating from various rotation positions of the workpiece are combined, for which:
the workpiece is rotated, with the aid of relative rotational and translational movements between the workpiece and the X-ray detector, about an axis of rotation different from the physical axis of rotation, such that at least a portion of the workpiece is constantly imaged at approximately the same position on the detector, and
at least one of the workpiece, the X-ray, and X-ray detector occupy several positions relative to one another.

2. The method according to claim 1, wherein the physical axis of rotation relative to the X-ray detector and the X-ray source is not fixed, and wherein the physical axis of rotation is moved in at least one translational direction or the physical axis of rotation is moved in at least one translational direction, and the X-ray detector is moved in at least one translational direction or at least one rotational direction and one translational direction.

3. The method according to claim 1, wherein the X-ray detector is fixed and the physical axis of rotation is moved in two translational directions, in which the first direction runs nearly perpendicular to the plane of the X-ray detector and the second direction is nearly perpendicular to the direction of the physical axis of rotation and nearly perpendicular to the normal to the plane of the X-ray detector.

4. The method according to claim 1, wherein the workpiece is rotated about the physical axis of rotation not fixed relative to at least one of the X-ray detector and the X-ray source, and wherein the physical axis of rotation is moved in a translational direction that runs nearly perpendicular to the plane of the X-ray detector, and the X-ray detector is moved in a direction running in the plane of the X-ray detector, which is perpendicular to the direction of the physical axis of rotation.

5. The method according to claim 4, wherein the X-ray detector is rotated about a direction that is nearly parallel to the physical axis of rotation or the measurement results are corrected taking into consideration the transmission of the workpiece that is off-center relative to at least one of an illumination and a current rotation of the X-ray detector with respect to the illumination.

6. The method according claim 1, wherein the axis of rotation differing from the physical axis of rotation is the virtual axis of rotation of the workpiece.

7. The method according claim 6, wherein virtual axis is the axis of symmetry of the workpiece.

8. The method according to claim 6, wherein measurement occurs without prior alignment of the workpiece to the physical axis of rotation and during the rotational motion of the physical axis of rotation, a translational motion occurs of the physical axis of rotation or of the X-ray detector and the physical axis of rotation, the virtual axis of rotation always remains centrically aligned in relation to the X-ray detector due to an alignment in advance of or during the actual measurement.

9. The method according to claim 8, wherein the alignment in advance of or during the actual measurement is achieved with the aid of a CNC-controlled coordinate axis.

10. The method according to claim 6, wherein a control computer determines the relative position of the virtual axis of rotation to the physical axis of rotation in space and therewith controls the combination for translational and rotational motions, by recording control measurements in the form of transmission images in at least two rotation positions assumed prior to or between the measurements proper at various rotation positions, and the physical axis of rotation is recorded, from which the respective position of the virtual axis of rotation is determined to the physical axis of rotation or for a position of a body characterizing the physical axis of rotation, in at least one coordinate, and the results of the respective control measurements are combined, or the position of the virtual axis of rotation for the physical axis of rotation is determined by a sensor before or during the measurement.

11. The method according to claim 6, wherein transmission images are each recorded only when predetermined angles are reached around the virtual axis of rotation.

12. The method according to claim 6, wherein in at least one of a plurality of relative positions between at least one of the workpiece, X-ray source, and X-ray detector, a part of the workpiece is not completely imaged at the X-ray detector in at least one rotation position, wherein this part of the workpiece that is perpendicular to the virtual axis of rotation departs from the available measurement area, and missing measurement values in the transmission images recorded are calculated from the measurement values of transmission images with the same rotation position.

13. The method according to claim 12, wherein representation and evaluation of the measurement values of transmission images occur in a common raster in space, taking into consideration the positions of at least one of the workpiece, X-ray source, and X-ray detector.

14. The method according to claim 13, wherein determining the common raster in space occurs using volumetric data that would be produced at a highest magnification.

15. The method according to claim 13, wherein measurement values for the common raster are determined by at least one of a merging and resampling method.

16. The method according to claim 1, wherein the physical axis of rotation moves on a smooth, closed curve about the virtual axis of rotation or in a straight line.

17. The method according to claim 16, wherein the physical axis of rotation runs in an elliptical path or in a circular path.

18. The method according to claim 1, wherein the physical axis of rotation runs perpendicular to the plane of the X-ray detector.

19. The method according to claim 1, wherein at least one of structures and geometries of at least one of rotationally symmetrical parts, tools, and tomography-capable parts can be determined.

20. The method according to claim 1, wherein the transmission images recorded at a plurality of relative positions between at least one of the workpiece, X-ray source, and X-ray detector are first reconstructed for each combination of relative positions for a volumetric data set, wherein these can partially overlap in order to subsequently be represented in a common raster in space and be able to be evaluated.

21. The method according to claim 1, wherein a measurement area is produced by means of various relative positions between at least one of the workpiece, X-ray source, and X-ray detector, which is larger than a measurement area covered by a fixed X-ray detector.

22. The method according to claim 21, wherein a relative movement between the workpiece and at least the X-ray detector occurs in at least one direction that is nearly perpendicular to the imaging axis.

23. The method according to claim 1, wherein the method is incorporated into a coordinate-measuring device.

24. An arrangement for determining structures, geometry, or both, of a workpiece by means of a computed-tomography measuring system, comprising at least an X-ray source, an X-ray detector, and a physical axis of rotation of a rotating support on which the workpiece is stationarily arranged, wherein the workpiece is rotatable, with the aid of a combination of relative rotational and translational motions between the workpiece and the X-ray detector, about an axis of rotation different from the physical axis of rotation such that at least a portion of the workpiece is constantly imaged at approximately the same position on the detector.

25. The arrangement according to claim 24, wherein at least one of:

the physical axis of rotation is movable in at least one translational direction, and the workpiece is arranged movable in at least one translational direction at the physical axis of rotation, and the X-ray detector is movable on at least one the translational and rotational axis.

26. The arrangement according to claim 24, wherein the physical axis of rotation is movable in two translational directions, wherein the first direction runs nearly perpendicular to a plane of the X-ray detector and the second direction runs nearly perpendicular to a direction of the physical axis of rotation and nearly perpendicular to a normal to the plane of the X-ray detector.

27. The arrangement according to claim 24, wherein the physical axis of rotation is movable nearly perpendicular to a plane of the X-ray detector and the X-ray detector is movable in at least one of the directions running in the plane of the X-ray detector, which runs nearly perpendicular to a direction of the physical axis of rotation.

28. The arrangement according to claim 27, wherein the X-ray detector is rotatable about an axis that runs nearly parallel to the axis of rotation.

29. The arrangement according to claim 24, wherein the arrangement is integrated into a coordinate-measuring device.

* * * * *